US008846941B2

(12) United States Patent
Kwiatkowski

(10) Patent No.: US 8,846,941 B2
(45) Date of Patent: Sep. 30, 2014

(54) FUNCTIONALIZED POLYMERS

(75) Inventor: Marek Kwiatkowski, Uppsala (SE)

(73) Assignee: QuiaPEG AB, Stockholm (SE)

(*) Notice: Subject to any disclaimer, the term of this patent is extended or adjusted under 35 U.S.C. 154(b) by 202 days.

(21) Appl. No.: 13/324,872

(22) Filed: Dec. 13, 2011

(65) Prior Publication Data
US 2012/0178940 A1 Jul. 12, 2012

(30) Foreign Application Priority Data

Dec. 13, 2010 (SE) ..................................... 1001187

(51) Int. Cl.
C07F 9/06 (2006.01)
C07F 9/6506 (2006.01)
C07F 9/572 (2006.01)
C07F 9/165 (2006.01)
C07F 9/09 (2006.01)
A61K 47/48 (2006.01)
C07F 9/24 (2006.01)
C08G 81/00 (2006.01)
C07F 9/6561 (2006.01)
C07F 9/655 (2006.01)

(52) U.S. Cl.
CPC .............. C08G 81/00 (2013.01); C07F 9/1653 (2013.01); C07F 9/094 (2013.01); C07F 9/091 (2013.01); A61K 47/48215 (2013.01); C07F 9/5721 (2013.01); C07F 9/2408 (2013.01); C07F 9/2458 (2013.01); C07F 9/6561 (2013.01); C07F 9/1651 (2013.01); C07F 9/65515 (2013.01); C07F 9/2475 (2013.01)
USPC ............................. 548/113; 548/413; 564/12

(58) Field of Classification Search
USPC ..................... 548/113, 413; 564/12
See application file for complete search history.

(56) References Cited

U.S. PATENT DOCUMENTS

| 4,647,447 | A | 3/1987 | Gries et al. |
| 5,922,897 | A | 7/1999 | Hu et al. |
| 6,165,501 | A | 12/2000 | Tirosh et al. |
| 6,320,041 | B1 | 11/2001 | Hogrefe et al. |
| 2003/0165849 | A1 | 9/2003 | Zhang et al. |
| 2006/0063147 | A1 | 3/2006 | Chernov et al. |
| 2006/0079486 | A1 | 4/2006 | Zalipsky |
| 2007/0276139 | A1 | 11/2007 | Song et al. |
| 2010/0240730 | A1 | 9/2010 | Beigelman et al. |
| 2014/0030278 | A1 | 1/2014 | Kwiatkowski |

FOREIGN PATENT DOCUMENTS

| JP | 10175987 | 6/1998 |
| WO | WO 02/083954 | 10/2002 |
| WO | WO 2004/030617 | 4/2004 |
| WO | WO 2004/073620 | 9/2004 |
| WO | WO 2007/059912 | 5/2007 |

OTHER PUBLICATIONS

International Preliminary Report on Patentability in International Application No. PCT/IB2011/003206, mailed Jun. 27, 2013, 12 pages.
Authorized Officer A. Van Der Heijden. International Search Report and Written Opinion in International Application No. PCT/IB2011/003206, dated Jun. 19, 2012, 18 pages.
Ananda et al., "Analysis of functionalization of methoxy-PEG as maleimide-PEG," Anal. Biochem., 2008, 374:231-242.
Ansel Introduction to Pharmaceutical Dosage Forms, Fourth Edition 1985, 126.
Atherton et al., "The Fluorenylmethoxycarbonyl Amino Protecting Group," in The Peptides, S. Udenfriend and J. Meienhofer, Academic Press, New York, 1987, 40 pages.
Blom et al., "Preparative LC-MS Purification: Improved Compound Specific Method Optimization," J. Combi. Chem., 2004, 6:874-883.
Conolly et al., "Chemical synthesis of oligonucleotides containing a free sulphydryl group and subsequent attachment of thiol specific probes," Nucleic Acids Res., 1985, 13(12):4485-4502.
Conrad et al., "Studies on the stability of trialkyl phosphates and di-(2'deoxythymidine) phosphotriesters in alkaline and neutral solution. A model study for hydrolysis of phosphotriesters in DNA and on the influence of β hydroxyethyl ester group," Chem. Bio. Interactions, 1986, 60:57-65.
Drioli et al., "Pure, homo-bifunctional poly(ethylene glycol) orthogonally protected: synthesis and characterisation," Reactive & Functional Polymers, 2001, 48:119-128.
Fee et al., "PEG-proteins: Reaction engineering and separation issues," Chemical Engineering Science, 2006, 61:924-934.
Fidanza et al., "Functionalization of Oligonucleotides by the Incorporation of Thio-Specific Report Groups," Methods in Molecular Biology, 1994, 26, 121-143.
Garegg et al., "Nucleoside hydrogenphosphonates in Oligonucleotide Synthesis," Chem. Scr., 1986, 26:59-62.
Gaur, "Introduction of 5'-Terminal Amino and Thiol Groups into Synthetic Oligonucleotides," Nucleosides, Nucleotides & Nucleic Acids, 1991, 10(4):895-909.
Hann et al., "1,3-Anhydro-2,4-methylene-D,L-xylitol and Related Compounds," J. Am. Chem. Soc., 1950, 72:561-566.
Hecker et al., "Prodrugs of Phosphates and Phosphonates," J. Med. Chem., 2008, 51:2328-2345.
Hoey et al., "Chemistry of X-Ray Contrast Media," Handbook of Experimental Pharmacology, 1984, 73:23-125.
Hovinen et al., "Versatile Strategy for Oligonucleotide Derivatization. Introduction of Lanthanide(III) Chelates to Oligonucleotides," Organic Lett., 2001, 3(16):2473-2476.
Jagur-Grudzinski, "Biomedical application of functional polymers," Reactive & Functional Polymers, 1999, 39:99-138.
Kachalova et al., "A New and Efficient Method for Synthesis of 5'Conjugates of Oligonucleotides through Amide-Bond Formation on Solid Phase," Helv. Chim. Acta, 2002, 85:2409-2416.
Khomutov, "Derivatives of Hydroxylamine, Synthesis of o-substituted hydroxylamines," Journal of General Chemistry 1961, 31:1992-1995.

(Continued)

Primary Examiner — Joseph Kosack
(74) Attorney, Agent, or Firm — Fish & Richardson P.C.

(57) ABSTRACT

This document relates to functionalized (e.g., mono- or bi-functional) polymers (e.g., polyethylene glycol and related polymers) as well as methods and materials for making and using such functionalized polymers.

35 Claims, No Drawings

(56) References Cited

OTHER PUBLICATIONS

Krempsky et al., "Biotin and fluorescein labeling of biomolecules by active esters of 1-phenypyrazolin-5-ones," *Tet. Lett.*, 1996, 37(12):4313-4316.

McGuigan et al., "Synthesis and biological evaluation of some phosphate triester derivatives of the anti-viral drug AraA," *Nucl. Acids Res.*, 1989, 17(15):6065-6075.

Petursson et al., "Protecting Groups in Carbohydrate Chemistry," *J. Chem. Educ.*, 1997, 74(11):1297.

Podyminogin et al., "Attachment of benzaldehyde-modified oligodeoxynucleotide probes to semicarbazide-coated glass," *Nucl. Acids Res.*, 2001, 29(24):5090-5098.

Raddetz et al., "Hydrazide oligonucleotides: new chemical modification for chip array attachment and conjugation," *Nucleic Acids Res.*, 2002, 30(21):4793-4802.

Rayudu, *Radiotracers for Medical Applications*, vol. I, pp. 201, 1983.

Remington's Pharmaceutical Sciences, 19th Edition (Mack Publishing Company, 1995 (Table of Contents only).

Roberts et al., "Chemistry for peptide and protein PEGylation," *Advanced Drug Delivery Reviews*, 2002, 54:459-476.

Sakaitani et al., "One-pot Conversion of N-Benzyloxycarbonyl Group into N-Tert-Butoxycarbonyl Group," *Tetrahedron Lett.*, 1988, 29:2983.

Singh et al. "New Method to Prepare Peptide-Oligonucleotide Conjugates through Glyoxylic Oxime Formation," *J. Org. Chem.*, 2004, 69:8544-8546.

Spinelli et al. "Aldehydic Oligonucleotide: A Key Intermediate for the Preparation of Oligonucleotide Conjugates Through Oxime Bond Formation," *Nucleosides, Nucleotides and Nucleic Acids*, 2007, 26:883-887.

Stahl et al., "General Procedure for the Synthesis of Mono-N-acylated 1,6-Diaminohexanes," *J. Org. Chem.*, 1978, 43:2285.

Swanson, "Enhancement Agents for Ultrasound: Fundamentals," *Pharmaceuticals in Medical Imaging*, 1990, pp. 682-687.

Tyler et al., "In Vivo Enhancement of Ultrasonic Image Luminance by Aqueous Solutions with High Speed of Sound," *Ultrasonic Imaging*, 1981, 3:323-29.

Zwierzak et al., "Phosphorous acid amides-II: Synthesis of momoalkyl phosphoroamidites $(RO)(R_2'N)P(O)H$," *Tetrahedron*, 1967, 23:2243-2252.

Invitation to Pay Addition Fees and, Where Applicable, Protest Fee in International Application No. PCT/IB2013/001885, mailed Mar. 3, 2014, 7 pages.

Ducreux et al., "The Inhibitory Potencies of Monoclonal Antibodies to the Macrophage Adhesion Molecule Sialoadhesin Are Greatly Increased Following PEGylation," Bioconjugate Chem., 2008, 19:2088-2094.

Tao et al., "α-Aldehyde Terminally Functional Methacrylic Polymers from Living Radical Polymerization: Application in Protein Conjugation 'Pegylation'," *J. Am. Chem. Soc.*, 2004, 126:13220-13221.

FUNCTIONALIZED POLYMERS

CLAIM OF PRIORITY

This application claims priority to Swedish Patent Application Serial No. 1001187-2, filed on Dec. 13, 2010, the entire contents of which are hereby incorporated by reference.

TECHNICAL FIELD

This document relates to functionalized (e.g., mono- or bi-functional) polymers (e.g., polyethylene glycol and related polymers) as well as methods and materials for making and using such functionalized polymers.

BACKGROUND

Pharmacokinetic and immune stimulating properties of proteins and synthetic drugs may be controlled by their conjugation to certain polymers. For example, polyethylene glycol (PEG) can be conjugated to proteins to achieve this effect (Fee and Van Alstine, *Chemical Engineering Science*, 61:924-934 (2006)). Such conjugation can take place if the relatively non-reactive hydroxyl groups present in PEG molecules are substituted by other, more reactive moieties (Jagur-Grudzinski, *Reactive & Functional Polymers*, 39:99-138 (1999)). A standard, linear PEG molecule is chemically a diol, which could suggest that the process of PEG derivatization and purification of products should be trivial. However, the polymeric nature of this diol, together with its amphiphilic properties can make these manipulations difficult. In some cases, the typical laboratory process for separation of difficult reaction mixtures, silica gel-based flash column chromatography, can fail for PEG with molecular weight higher than 1000. Neither crystallization nor precipitation appear adequate to achieve separation of PEG-containing materials, even if these methods can be used for efficient removal of other, contaminating substances with low molecular weight. Most reaction mixtures containing modified PEG molecules lack a reliable analytical method to control or to prove their composition. Polymers with functions that influence only minimally the hydrophobic properties of the polymer can be difficult to analyze by chromatography. The same applies for polymers with functions carrying only a minimal charge. This also applies for preparative chromatographic separation of charged polymers as described elsewhere for the separation of mono- and di-carboxyl modified PEG molecules (Drioli et al., *Reactive & Functional Polymers*, 48:119-128 (2001)).

Confirmation of results of the synthesis based on NMR can be useless, as long as one is not sure about the purity of the product, and this is typically only obtained by chromatographic methods. This unusual conclusion comes from observations that an equimolar mixture of non-derivatized polymer and bis-derivatized polymer will produce an NMR pattern identical to the pure mono-derivatized polymer. Mass spectrometry can be complicated since most PEG exists not in the form of a single component, but is rather a Gaussian population of different polymer lengths, centered on its average molecular weight. Thus, even if all distinct components of the same type should have their mass increased by the same factor, the presence of unreacted and bis-modified material can obscure the picture of the analysis. The literature discusses this problem only sporadically, and often nothing is mentioned about analysis of the product or its purification. Many authors make the impression that the process that they describe is ongoing with quantitative yield, and thus the quality of the product does not need to be analyzed or questioned. This non-scientific approach can be frequently encountered in the chemistry of PEG. There are many examples in the literature presenting synthetic procedures with four to five consecutive steps without a single analysis of the product at any of these steps, without any attempts to purifying the product, and assuming 100 percent purity at the end of the process. It is, therefore, not strange that researchers after closer testing question these products and their purity (Ananda et al., *Anal. Biochem.*, 374, 231-242 (2008)). A commonly accepted escape from the problem of selective modification is to work with a polymer that has one end blocked from the beginning by a stable chemical group, most often a methoxy group (mPEG). In theory, this blockage converts a PEG molecule to a monofunctional compound, and as such, it could be fully converted to the second derivatized form by increasing the amount of derivatizing reagent and/or time for reaction. Unfortunately, many of reactions commonly applied for derivatization of PEG are sluggish and only seldom go to completion. On the other hand, mPEG preparations contain significant percentages of PEG diol component. Moreover, the amount of this contamination increases with the length of mPEG, and this contamination can be hard to avoid. Consequently, derivatization will also result in formation of symmetrical, bis-derivatizated PEG, and its presence in the conjugating mixture results in formation of cross-linked products with unknown pharmacologic properties or a possible loss of protein activity. Therefore, pure, monofunctional polymers are usually preferred for protein modification, but one should be aware that purification of mPEG from its diol PEG contamination is practically impossible.

Nearly all of existing reactions, used today for derivatization of PEG, belong either to the alkylation-based or the acylation-based category. In the first case, the alkoxy anion, generated from PEG, is reacting with incoming electrophilic modifying reagent. Eventually, the activated PEG, subjected with a good leaving group, is itself an object of a nucleophilic attack. To this category belong processes resulting in thiolation, amination, azidation, and introduction of a carboxyl or an aldehyde group. Modified PEG's of this category will have their functional group connected directly to the PEG terminal carbon atom or these groups will be linked via an ether bond, a thioether bond, or a secondary amino group.

The second category, acylation, is based on a nucleophilic reaction of PEG's hydroxyl, (or another group present in a modified PEG—often an amino group), on an incoming acylating reagent. In many cases, this first acylation is followed by a second acylation that actually introduces the modification of interest to the PEG molecule. Functional groups incorporated by this method can be linked to the rest of PEG by an amido, a carbamido, urethane, thiourethane, or a simple ester group. These linking groups and the chemistry behind them belong to the very traditional methods of combining two chemical identities.

Polyethylene glycols (PEG) coupled to phosphoramidites are used for direct coupling of PEG molecules to synthetic nucleic acids. One example is 4,4'-dimethoxy-trityl-polyethyleneglycol-[(2-cyanoethyl)-(N,N-diisopropyl)]-phosphoramidite. In these compounds, the phosphoramidite group is the part of the reactive functionality for linking the compound to a synthetic nucleic acid. It is designed to work in a completely water-free environment: In the presence of water, the phosphoramidite group can decompose instantaneously, making such PEG phosphoramidites inappropriate for conjugation to biological material in water-containing or aqueous solution. In particular, these PEG phosphoramidites can be inappropriate for conjugation to biological substances which are not soluble, stable or sufficiently reactive in non-aqueous media.

Furthermore, already mildly acidic biological substances can decompose these PEG phosphoramidites. Finally, these PEG phosphoramidites contain a labile protecting group adjacent to the phosphorous atom which is specially designed to convert the intermediate phosphotriester to a phosphodiester. Phosphodiesters can be readily degraded enzymatically in vivo.

SUMMARY

This document provides functionalized (e.g., mono- or bi-functional) polymers (e.g., polyethylene glycol and related polymers) as well as methods and materials for making and using such functionalized polymers. The functionalized polymers can be used to conjugate a biologically active molecule, thereby potentially altering the pharmacokinetic and pharmacodynamic profile of the biologically active molecule. The functionalized polymers include one or more linking groups selected from a phosphotriester, a phosphoramidate, a thiophosphotriester, and a thiophosphoramidate. For example, this document provides a PEG polymer having at least one terminus covalently bound to a phosphotriester or phosphoramidate linking group. A functionalized polymer provided herein can include different linking groups at each of its termini. Also provided herein is a functionalized polymer modified at least one terminus with a blocking group (e.g., methoxy group) and functionalized at least another terminus with a linking group as described herein.

As described herein, preparations of a functionalized polymer having one or more linking groups can be obtained in a manner where greater than 50 percent by weight (e.g., greater than 75 percent, greater than 80 percent, greater than 90 percent, greater than 95 percent, greater than 98 percent, and greater than 99 percent by weight) of the preparation is the desired functionalized polymer free from contaminants. As a person of ordinary skill in the art would understand, a functionalized polymer preparation includes a Gaussian population of different polymer lengths centered on an average molecular weight, and such a functionalized population would not be considered contaminating. For example, a mono-functionalized PEG population can be separated nearly quantitatively from contaminants of PEG functionalization (e.g., unreacted PEG and poly-functionalized PEG populations). The separation of a functionalized polymer provided herein can be facilitated through the use of a removable hydrophobic separation handle (e.g., a substituted or unsubstituted trityl group) which upon removal allows for preparative isolation of product (e.g., pure product), free or substantially free from unreacted polymer and poly-functionalized polymer.

Having the ability to isolate functionalized polymers in high purity can allow chemists to more easily control subsequent reactions or the purity of the downstream products. In some cases, having the ability to introduce all functional groups through a unified process using similar, mild reagents and reaction conditions can allow for the production of a functionalized polymer through a fast and nearly quantitative reaction.

The ability to isolate functionalized polymers quantitatively can allow chemists to more easily control subsequent reactions or the purity of conjugates of a biologically active molecule coupled to a functionalized polymer provided herein.

In addition to increasing the purity of a functionalized polymer, a linking group can act as a linker between the polymer and a biologically active group or a detectable functional group. For instance, a functionalized polymer of high purity can be coupled to a biologically active molecule or a detectable functional group. In such conjugates, the linker can form covalent bonds to the polymer and a biologically active molecule or a detectable functional group. The coupling can take place in an aqueous reaction medium. The biologically active molecule or detectable functional group can be acidic.

Furthermore, the linking groups provided herein are generally resistant to chemical and enzymatic degradation, providing for more stable storage and increased safety and efficacy in vivo.

Provided herein is a compound comprising a water-soluble, non-peptidic, and non-nucleotidic polymer backbone having at least one terminus covalently bonded to a structure of formula (1):

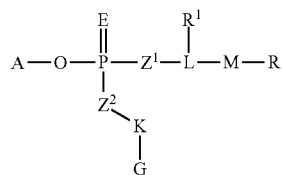

or a salt thereof,
wherein:
A is the point of covalent bonding to the terminus of the polymer backbone;
E is O or S;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently selected from O and NH, wherein only one of $Z^1$ and $Z^2$ can be NH;
L is selected from the group consisting of: a divalent radical of a nucleoside, alkylene, alkyleneoxyalkylene, oligomeric alkyleneoxyalkylene, and unsubstituted and substituted arylene;
M is a protected group that when deprotected is reactive with a biologically active molecule, a group reactive with a biologically active molecule, or is a detectable functional group;
R is absent or selected from the group consisting of: hydrogen, a protecting group, a hydrophobic separation handle, or an activating group;
$R^1$ is absent or a hydrophobic separation handle;
wherein when M is a protected group that when deprotected is reactive with a biologically active molecule, then R is a protecting group or a hydrophobic separation handle;
wherein when M is a group reactive with a biologically active molecule, R is absent, hydrogen, or an activating group; and
wherein when M is a detectable functional group, R is absent or hydrogen.

In some embodiments, at least one of R, $R^1$, and G is a hydrophobic separation handle. For example, only one of R, $R^1$, and G can be a hydrophobic separation handle. In some embodiments, the hydrophobicity of one of R or $R^1$ is higher than the other.

In some embodiments, the polymer backbone has from 2 to 100 termini. In some embodiments, only one termini of the polymer backbone is covalently bonded to the structure of formula (1).

In some embodiments, the polymer backbone has two termini. In some embodiments, only one termini of the polymer backbone is covalently bonded to the structure of formula (1). In some embodiments, both termini of the polymer backbone are covalently bonded to the structure of formula (1).

A polymer backbone can be selected from the group consisting of: poly(alkylene glycol), poly(oxyethylated polyol), poly(olefinic alcohol), poly($\alpha$-hydroxy acid), poly(vinyl alcohol), polyoxazoline, and copolymers. For example, a polymer backbone can be poly(ethylene glycol). In some cases, a poly(ethylene glycol) has an average molecular weight from about 500 Da to about 100,000 Da.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

A group reactive with a biologically active molecule can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

In some embodiments, K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G is a substituted or unsubstituted trityloxy.

In some embodiments, L is a substituted or unsubstituted $C_1$-$C_{12}$ alkylene.

In some embodiments, R is selected from the group consisting of: trityl, monoalkoxytrityl, dialkoxytrityl, pixyl, alkoxypixyl, fluorenylmethyloxycarbonyl, trifluoroacetyl, acetal, and cyclic acetal.

In some embodiments, a group reactive with a biologically active molecule is carboxyl and R is absent or selected from the group consisting of: chlorotrityl, trityl, N-hydroxysuccinimidyl, p-nitrophenyl, pentachlorophenyl, and an unsubstituted $C_1$-$C_{18}$ alkyl.

Also provided herein is a preparation comprising a compound comprising a water-soluble, non-peptidic, and non-nucleotidic polymer backbone having at least one termini covalently bonded to a structure of formula (1):

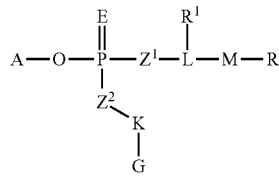

or a salt thereof, wherein the preparation comprises at least 50% by weight of the compound. In some embodiments, the compound is essentially pure.

Further provided herein is a method for making a compound of claim 1, said method comprising: contacting a water-soluble, non-peptidic, and non-nucleotidic polymer, in a water-free solvent, with a reagent of formula (4):

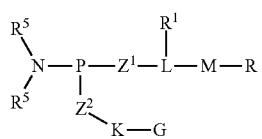

wherein:
$R^5$ and $R^6$ independently from each other represent $C_1$-$C_6$-alkyl or $R^5$ and $R^6$ jointly form a 5- or 6-membered ring with the N to which they are bonded;

adding an activating reagent; and adding an oxidizing reagent, wherein the P is oxidized from $P^{+3}$ to $P^{+5}$.

In some embodiments, R is a protecting group.

In some embodiments, the method further comprises purifying the protected polymer by chromatography. In some embodiments, the method further comprises removing the protecting group.

An activating reagent can be selected from the group consisting of: tetrazole, 2-ethylthiotetrazole, 2-bezylthiotetrazole, 4,5-dicyanoimidazole, Activator 42, pyridinium hydrochloride, and pyridinium trifluoroacetate. An oxidizing reagent can be selected from a group consisting of: iodine, hydrogen peroxide, t-butyl hydrogen peroxide, acetone peroxide, sulfur, and thiuram disulfide. In some embodiments, the ratio of the polymer to the compound of formula (4) is from about 1:10 to about 10:1.

A compound provided herein can be used in a conjugate, or a pharmaceutically acceptable salt thereof, comprising a compound and a biologically active molecule. Such a conjugate can be prepared by conjugating the compound to a biologically active molecule.

Provided herein is a compound of formula (2):

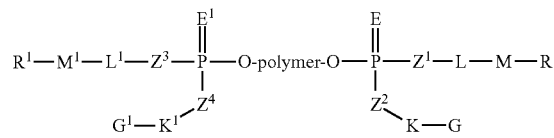

or a salt form thereof,
wherein:
polymer is a linear, water-soluble, non-peptidic, and non-nucleotidic polymer backbone, wherein each linking group is bonded at a different terminus of said polymer;
E and $E^1$ are independently O or S;
K and $K_1$ are independently selected from the group consisting of: alkylene, alkyleneoxyalkylene, and oligomeric alkyleneoxyalkylene;
G and $G_1$ are independently absent or are selected from the group consisting of: alkoxy and a hydrophobic separation handle;
each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH;
L and $L^1$ are independently selected from the group consisting of: a divalent radical of a nucleoside, alkylene, alkyleneoxyalkylene, oligomeric alkyleneoxyalkylene, and unsubstituted and substituted arylene;
M and $M^1$ are independently selected from a protected group that when deprotected is reactive with a biologically active molecule, a group reactive with a biologically active molecule, or is a detectable functional group, wherein M and $M^1$ are different; and
R and $R^1$ are independently absent, hydrogen, a protecting group, or an activating group;
wherein when M is a protected group that when deprotected is reactive with a biologically active molecule, then R is a protecting group or a hydrophobic separation handle;
wherein when M is a group reactive with a biologically active molecule, R is absent, hydrogen, or an activating group;

wherein when M is a detectable functional group, R is absent or hydrogen;
wherein when $M^1$ is a protected group that when deprotected is reactive with a biologically active molecule, then $R^1$ is a protecting group or a hydrophobic separation handle;
wherein when $M^1$ is a group reactive with a biologically active molecule, $R^1$ is absent, hydrogen, or an activating group; and
wherein when $M^1$ is a detectable functional group, $R^1$ is absent or hydrogen.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O. In some embodiments, one of $Z^3$ and $Z^4$ is NH and the other is O. In some embodiments, $Z^3$ is O and $Z^4$ is NH. In some embodiments, $Z^3$ is NH and $Z^4$ is O. In some embodiments, both $Z^3$ and $Z^4$ are O.

In some embodiments, a group reactive with a biologically active molecule is independently selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

In some embodiments, K and $K^1$ are independently selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G and $G^1$ is independently selected from a substituted or unsubstituted trityloxy.

In some embodiments, L and $L^1$ is independently a substituted or unsubstituted $C_1$-$C_{12}$ alkylene.

In some embodiments, R or $R^1$ is independently selected from the group consisting of: trityl, monoalkoxytrityl, dialkoxytrityl, pixyl, alkoxypixyl, fluorenylmethyloxycarbonyl, trifluoroacetyl, acetal, cyclic acetal, and combinations of thereof.

In some embodiments, the polymer is poly(ethylene glycol). For example, a poly(ethylene glycol) having an average molecular weight from about 500 Da to about 100,000 Da.

Also provided herein is a preparation comprising a compound of formula (2):

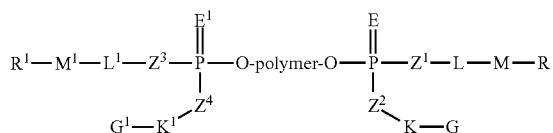

or a salt form thereof, wherein the preparation comprises at least 50% by weight of the compound.

Further provided herein is a method for making a compound of formula (2), the method comprising: reacting a linear, water-soluble, non-peptidic, and non-nucleotidic polymer, in a water free solvent, with a reagent selected from the group consisting of a compound of formula (5):

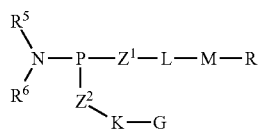

wherein:
$R^5$ and $R^6$ independently from each other represent $C_1$-$C_6$-alkyl or jointly form a 5- or 6-membered ring, and a compound of formula (6):

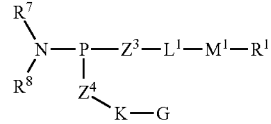

wherein:
$R^7$ and $R^8$ independently from each other represent $C_1$-$C_6$-alkyl or $R^7$ and $R^8$ jointly form a 5- or 6-membered ring with the N to which they are bonded;
under conditions that facilitate formation of monoderivatized product; and
reacting the monoderivatized product with a reagent selected from the group consisting of a compound of formula (5) and a compound of formula (6), wherein the reagent is different from the reagent from step a); under conditions that facilitate conversion to the compound.

In some embodiments, the method further comprises isolating the monoderivatized product using by chromatography prior to reacting the monoderivatized product.

In some embodiments, the conversion to the compound is quantitative.

In some embodiments, R is a hydrophobic separation handle. In some embodiments, the method further comprises removing the hydrophobic separation handle and isolating the compound by precipitation or crystallization.

A compound of formula (2) provided herein can be used in a conjugate, or a pharmaceutically acceptable salt thereof, comprising a compound and a biologically active molecule. Such a conjugate can be prepared by conjugating the compound to a biologically active molecule.

Also provided herein is a compound of formula (3):

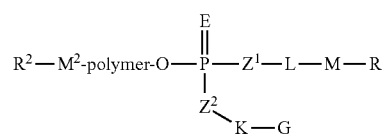

or a salt form thereof,
wherein:
polymer is a linear, water-soluble, non-peptidic, and non-nucleotidic polymer backbone, wherein $M^2$ and the phosphonate-derived functional group are bonded at a different terminus of said polymer;
E and $E^1$ are independently O or S;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently selected from O and NH, wherein only one of $Z^1$ and $Z^2$ can be NH;
L is selected from the group consisting of: a divalent radical of nucleoside, alkylene, alkyleneoxyalkylene, oligomeric alkyleneoxyalkylene, and unsubstituted and substituted arylene;
M is selected from a protected group that when deprotected is reactive with a biologically active molecule, a group reactive with a biologically active molecule, or is a detectable functional group;

$M^2$ is selected from O, S or NH; and

R is absent, a protecting group, a hydrophobic separation handle, or an activating group;

$R^2$ is hydrogen or a protecting group;

wherein when M is a protected group that when deprotected is reactive with a biologically active molecule, then R is a protecting group or a hydrophobic separation handle;

wherein when M is a group reactive with a biologically active molecule, R is absent, hydrogen, or an activating group; and wherein when M is a detectable functional group, R is absent or hydrogen.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

A group reactive with a biologically active molecule can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

In some embodiments, K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G is a substituted or unsubstituted trityloxy. For example, G can be a monoalkoxy substituted trityloxy group or a dialkoxy substituted trityloxy group.

In some embodiments, $R^2$ is absent or selected from the group consisting of trityl, monoalkoxytrityl, dialkoxytrityl, pixyl, alkoxypixyl, fluorenylmethyloxycarbonyl, alkylcarboxyl, benzoyl, tetrahydropyranyl, methyl.

In some embodiments, the polymer is poly(ethylene glycol).

Further provided herein is a preparation comprising a compound of formula (3):

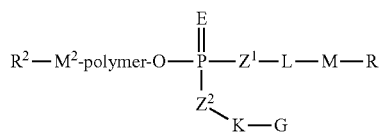

or a salt form thereof, wherein said preparation comprises at least 50% of said compound.

A compound of formula (3) can be prepared by reacting a monosubstituted polymer comprising a linear, water-soluble, non-peptidic, and non-nucleotidic polymer backbone bonded at the first terminus with the functional group $M^2$-$R^2$, with a reagent of formula (5):

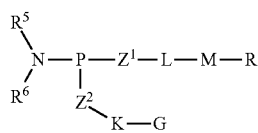

wherein:

$R^5$ and $R^6$ independently from each other represent $C_1$-$C_6$-alkyl or $R^5$ and $R^6$ jointly form a 5- or 6-membered ring with the N to which they are attached; under conditions facilitating the quantitative conversion of said monosubstituted polymer to said compound.

In some embodiments, the compound of formula (3) is isolated by precipitation or crystallization.

In some embodiments, R is a hydrophobic separation handle.

In some embodiments, the method further comprises removal of the hydrophobic separation handle and isolating said compound by precipitation or crystallization.

A compound of formula (3) provided herein can be used in a conjugate, or a pharmaceutically acceptable salt thereof, comprising a compound and a biologically active molecule. A biologically active molecule can be selected from the group consisting of enzymes, peptides, polypeptides, nucleotides, oligonucleotides, polynucleotides, and therapeutic agents having a molecular weight of less than 1000 g/mol. Such a conjugate can be prepared by conjugating the compound to a biologically active molecule.

Provided herein is a method of preparing a compound comprising a water-soluble, non-peptidic, and non-nucleotidic polymer backbone having at least one terminus covalently bonded to a structure of formula (7):

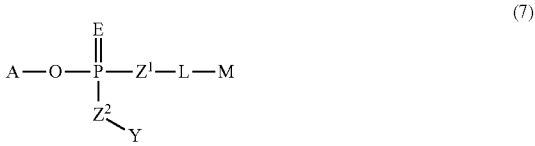

or a salt thereof, wherein:

A is the point of covalent bonding to the terminus of the polymer backbone;

E is O or S;

Y represents an optionally substituted residue selected from alkyl, cycloalkyl, heterocyclyl, aryl, and heteroaryl;

$Z^1$ and $Z^2$ are independently selected from O and NH, wherein only one of $Z^1$ and $Z^2$ can be NH;

L is selected from the group consisting of: a divalent radical of a nucleoside, alkylene, alkyleneoxyalkylene, oligomeric alkyleneoxyalkylene, and unsubstituted and substituted arylene;

M is a biologically active molecule or a detectable functional group;

comprising the steps of:

providing a compound of formula (8):

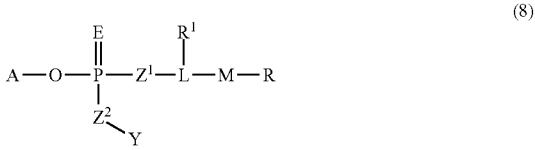

wherein:

A is the point of covalent bonding to the terminus of the polymer backbone;

E is O Or S;

Y represents an optionally substituted residue selected from alkyl, cycloalkyl, heterocyclyl, aryl, and heteroaryl;

$Z^1$ and $Z^2$ are independently selected from O and NH, wherein only one of $Z^1$ and $Z^2$ can be NH;

L is selected from the group consisting of: a divalent radical of a nucleoside, alkylene, alkyleneoxyalkylene, oligomeric alkyleneoxyalkylene, and unsubstituted and substituted arylene;

M is a protected group that when deprotected is reactive with a biologically active molecule;

R is a hydrophobic separation handle;

$R^1$ is absent or a hydrophobic separation handle; and (b) removing the hydrophobic separation handle(s);

(c) optionally reacting the compound obtained in step (b) with an activating agent; and (d) reacting the compound obtained in step (b), or, optionally in step (c), with a biologically active material or the detectable functional group.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

The protected group M can be, when deprotected, selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

In some embodiments, R is selected from the group consisting of: trityl, monoalkoxytrityl, dialkoxytrityl, pixyl, alkoxypixyl, fluorenylmethyloxycarbonyl, trifluoroacetyl, acetal, and cyclic acetal.

In some embodiments, the polymer backbone is selected from the group consisting of poly(alkylene glycol), poly(oxyethylated polyol), poly(olefinic alcohol), poly(α-hydroxy acid), poly(vinyl alcohol), polyoxazoline, and copolymers. For example, the polymer backbone can be poly(ethylene glycol).

In some embodiments, reaction step (d) is carried out in the presence of water or a protic solvent. In some embodiments, the compound of formula (8) is essentially pure. In some embodiments, the biologically active material or the detectable functional group reacts acidic in water.

This disclosure utilizes phosphoramidites as reagents interacting with polymers to form a phosphotriester-type of linker between a polymer and linking group. A similar process is used commonly in the chemistry of nucleic acids. Formation of a phosphotriester bond, in the chemistry of nucleic acids, is often followed by its partial hydrolysis (deprotection) to the phosphodiester bond, because phosphodiester bonds are naturally occurring. The present disclosure provides an uncommon and unnatural phosphotriester linkage which is enzymatically resistant, offering a stable linker between a polymer and a biologically active molecule.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides functionalized (e.g., mono- or bi-functional) polymers (e.g., polyethylene glycol and related polymers) as well as methods and materials for making and using such functionalized polymers. The functionalized polymers can be used to conjugate a biologically active molecule, thereby potentially altering the pharmacokinetic and pharmacodynamic profile of the biologically active molecule. The functionalized polymers include one or more linking groups selected from a phosphotriester, a phosphoramidate, a thiophosphotriester, and a thiophosphoramidate. A functionalized polymer provided herein can include different linking groups at each of its termini. Also provided herein is a functionalized polymer modified at least one terminus with a blocking group (e.g., methoxy group) and functionalized at least another terminus with a linking group as described herein.

For example, this document provides functionalized PEG polymers. In some cases, a functionalized PEG polymer has at least one terminus covalently bound to a phosphotriester, a phosphoramidate, a thiophosphotriester, and a thiophosphoramidate linking group. For example, a functionalized PEG polymer can have at least one terminus covalently bound to a phosphotriester or phosphoramidate linking group.

In some cases, a PEG polymer is a linear PEG polymer (i.e., having two termini). A linear PEG polymer can be functionalized as described herein at one or both termini with the same or different linking groups. In some cases, one of the termini of a linear PEG polymer is blocked with a blocking group (e.g., methoxy or a protecting group) and the other termini is functionalized with a linking group as described herein. In some cases, one of the termini of a linear PEG polymer is functionalized with a phosphotriester linking group and the other termini is functionalized with a phosphoramidate linking group. In other cases, both termini are functionalized with the same or different phosphotriester linking groups. In yet other cases, both termini are functionalized with the same or different phosphoramidate linking groups.

DEFINITIONS

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). The term $C_{1-12}$ includes alkyl groups containing 1 to 12 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_{2-12}$ for straight chain; $C_{3-12}$ for branched chain). The term $C_{2-12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_{2-12}$ for straight chain; $C_{3-12}$ for branched chain). The term $C_{2-6}$ includes alkynyl groups containing 2 to 12 carbon atoms.

The term "alkylene" by itself or as part of another molecule means a divalent radical derived from a linear or branched alkane, as exemplified by $(-CH_2-)_n$, wherein n may be 1 to 24 (e.g., 1 to 20, 1 to 18, 1 to 16, 1 to 15, 1 to 12, 1 to 10, 1 to 8, 1 to 6, 1 to 5, 1 to 4, 1 to 3, 1 to 2, 2 to 24, 2 to 12, 2 to 8). By way of example only, such groups include, but are not limited to, groups having 10 or fewer carbon atoms such as the structures $-CH_2CH_2-$ and $-CH_2CH_2CH_2CH_2-$. A "lower alkyl" or "lower alkylene" is a shorter chain alkyl or alkylene group, generally having eight or fewer carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_{1-12}$ alkoxy). For example, $C_{1-10}$, $C_{1-8}$, $C_{1-6}$, $C_{1-4}$, $C_{1-3}$, $C_{1-2}$). Non-limiting examples of an alkoxy group include methoxy, ethoxy, propoxy, butoxy, and hexoxy.

The term "alkyleneoxyalkylene," as used herein, refers to a divalent radical derived from a linear or branched alkyloxyalkane, as exemplified, but not limited by, $-CH_2-CH_2-O-CH_2-CH_2-$ and $-CH_2-CH_2-O-$. By way of example only, such groups include, but are not limited to, groups having the formula $-(CH_2)_n-O-(CH_2)_m-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, to 50, 5 to 15, 2 to 12, 20 to 30, and 6 to 18) and m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18).

The term "oligomeric alkyleneoxyalkylene" refers to p-repetitive alkyleneoxyalkylene wherein p is an integer of between 2 and 24 (e.g., 2 to 20, 2 to 18, 2 to 16, 2 to 15, 2 to 12, 2 to 10, 2 to 8, 2 to 6, 2 to 5, 2 to 4, 2 to 3). By way of example only, such groups include, but are not limited to, groups having the formula $-((CH_2)_n-O-(CH_2)_m)_p-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In general, the term "arylene" by itself or as part of another molecule means a divalent radical derived from an aryl, including, for example, 5- and 6-membered single-ring aromatic groups, such as benzene and phenyl. Furthermore, the term "arylene" includes a divalent radical derived from a multicyclic aryl group, e.g., tricyclic, bicyclic, such as naphthalene and anthracene.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring.

Substituents include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, $-(CH_2)_m-O-(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, $-NO_2$, $-CN$, $-NR^9C(O)-(C_1$-$C_{10}$ alkyl), $-C(O)-(C_1$-$C_{10}$ alkyl), $C_2$-$C_{10}$ alkthioalkyl, $-C(O)O-(C_1$-$C_{10}$ alkyl), $-OH$, $-SO_2$, $=S$, $-COOH$, $-NR^9_2$, carbonyl, $-C(O)-(C_1$-$C_{10}$ alkyl)-$CF_3$, $-C(O)-CF_3$, $-C(O)NR^9_2$, $-(C_1$-$C_{10}$ aryl)-S-$(C_6$-$C_{10}$ aryl), $-C(O)-(C_6$-$C_{10}$ aryl), $-(CH_2)_m-O-(CH_2)_m-O-(C_1$-$C_{10}$ alkyl) wherein each m is from 1 to 8, $-C(O)NR^9_2$, $-C(S)NR^9_2$, $-SO_2NR^9_2$, $-NR^9C(O)NR^9_2$, $-NR^9C(S)NR^9_2$, salts thereof, and the like. Each $R^9$ group in the preceding list independently includes, but is not limited to, H, alkyl or substituted alkyl, aryl or substituted aryl, or alkylaryl. Where substituent groups are specified by their conventional chemical formulas, written from left to right, they equally encompass the chemically identical substituents that would result from writing the structure from right to left, for example, $-CH_2O-$ is equivalent to $-OCH_2-$.

The term "polymer backbone" refers to the main chain of a linear or branched polymer.

The term "water-soluble polymer backbone" refers to a polymer backbone having water-solubility or dispersibility in water at ambient temperatures and a pH of about 7. For instance, a polyethylene glycol backbone is considered to be water-soluble if the corresponding polyethylene glycol can be solubilized or dispersed in water at ambient temperatures and a pH of about 7.

The term "nucleotidic polymer" refers to a single- or double-stranded polymer chain composed of two or more nucleic acids. The term "nucleic acid" refers to deoxyribonucleotides or ribonucleotides. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidites, and the like); (iii) conservatively modified variants thereof (including but not limited to, degenerate codon substitutions) and complementary sequences.

The term "peptidic polymer" refers to a polymer of two or more amino acid residues. The term applies to naturally occurring amino acid polymers as well as amino acid polymers in which one or more amino acid residues is a non-natural amino acid.

As used herein, a "biologically active molecule" includes any molecule which can have a biological effect. Examples of biologically active molecules include therapeutic agents, small molecules, oligo- and polypeptides, oligonucleotides, coding DNA sequences, antisense DNA sequences, mRNAs, antisense RNA sequences, RNAis, and siRNAs, carbohydrates, lipids, growth factors, enzymes, transcription factors, toxins, antigenic peptides (as for vaccines), antibodies, and antibody fragments.

The term "group reactive with a biologically active molecule" refers to a functional group that can be covalently bound to a functional group of a biologically active molecule.

The terms "protecting group" and "protective group" refer to a moiety that reversibly chemically modifies a functional group in order to obtain chemoselectivity or in order to reduce degradation in one or more subsequent chemical reactions. Suitable protecting groups are well known in the art (see, e.g., Greene and Wuts, *Protective Groups in Organic Synthesis*, 3rd Ed., John Wiley & Sons, New York, N.Y., 1999, which is incorporated herein by reference in its entirety).

The term "detectable functional group" refers a functional group that physically or chemically interacts with its environment to produce a signal or product that can be detected by analytical and/or imaging methods such as visible, UV-, IR-, NIR-light, X-Ray, and NMR-based imaging methods, enzymatic assays, and UV-, IR-, NMR-, X-ray-, and mass spectrometry-based analytics.

As used herein, a "fluorophore" is a chemical group that can be excited by light to emit fluorescence. Some suitable fluorophores may be excited by light to emit phosphorescence. As used herein, a "dye" may include a fluorophore. Non-limiting examples of a fluorophore include: 1,5 IAEDANS; 1,8-ANS; 4-Methylumbelliferone; 5-carboxy-2, 7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMIA (5-Carboxytetranethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxy-acridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

Fluorophores may include derivatives that have been modified to facilitate conjugation to another reactive molecule. As such, fluorophores may include amine-reactive derivatives such as isothiocyanate derivatives and/or succinimidyl ester derivatives of the fluorophore.

The term "hydrophobic separation handle" refers to a moiety that when attached to or part of a compound reduces the hydrophilicity of that compound, i.e. reduces its tendency to be solved or dispersed in water. The term "separation handle" refers to a moiety that when attached to or part of a compound alters the mobility of that compound in a chromatographic method such that its separation from contaminants is improved. Alternatively, the term "separation handle" refers to a moiety that when attached to or part of a compound improves the yield of the compound in a chromatographic method in comparison to a hydrogen substituent.

The term "hydrophobicity" refers to the relative degree with which a compound or moiety is solved or dispersed in a non-aqueous solvent such as n-octanol. The degree of hydrophobicity or hydrophilicity of a compound or moiety can be measured using methods known in the art, such as, reversed phase chromatography and other chromatographic methods, partitioning, accessible surface area methods, and measurement of physical properties such as partial molar heat capacity, transition temperature and surface tension.

The term "activating group" refers to a moiety that increases the capability of the group reactive with a biologically active molecule to form a covalent bond with a biologically active molecule. Usually these groups increase or decrease the electronegativity of a selected moiety so it becomes more nucleophilic or more electrophilic. Non-limiting examples of an activating group include: lower alkylamino, diloweralkylamino, amino, halo, aryl, lower alkoxy, lower aralkoxy, aryloxy, mercapto, lower alkylthio, nitro, monophaloalkyl, dihaloalkyl, trihaloalkyl (e.g., $CF_3$), halo, formyl, lower alkanoyl, lower alkylsulfonyl, lower alkylsulfinyl, and the like.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. By way of example a preparation of a mono-functionalized compound may be "essentially pure" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating unfunctionalized and/or poly-functionalized polymers. An essentially pure compound may be obtained using chromatographic purification methods.

The term "protic solvent" is used herein to refer to solvents which comprise dissociable hydrogen ions. Examples of protic solvents include alcohols, such as ethanol, and methanol.

The phrase "pharmaceutically acceptable" is used herein to refer to those inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Some of the compounds provided herein are acidic and may form a salt with a pharmaceutically acceptable cation. Some of the compounds herein can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

Compounds
Compounds of Formula (1)

Provided herein is a compound comprising a water-soluble, non-nucleotidic and non-peptidic polymer backbone having at least one terminus covalently bonded to a structure of formula (1):

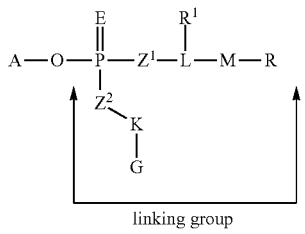

linking group or pharmaceutical salt thereof wherein: A is the point of bonding to a terminus of the polymer backbone, E is an oxygen or sulfur atom, K is selected from the group consisting of alkylene, alkyleneoxyalkylene, or an oligomeric form of alkyleneoxyalkylene, G is selected from the group consisting of hydrogen, an alkoxy, or a hydrophobic separation handle, $Z^1$ and $Z^2$ can be oxygen or nitrogen, in such way that both $Z^1$ and $Z^2$ may be oxygen, but when $Z^1$ is NH then $Z^2$ is oxygen, and when $Z^2$ is NH then $Z^1$ is oxygen, L is selected from the group consisting of a divalent radical of a nucleoside, linear alkylene, branched alkylene, alkyleneoxyalkylene, oligomeric form of alkyleneoxyalkylene, arylene, and substituted arylene, M is a protected group that when deprotected is reactive with a biologically active molecule, a group reactive with a biologically active molecule, or detectable functional group, R is a protecting group, activating group, hydrogen or absent.

A polymer backbone, as provided herein, can be branched or linear. For example, a polymer backbone can have from 2 to 100 termini (e.g., 2 to 80, 2 to 75, 2 to 60, 2 to 50, 2 to 40, 2 to 35, 2 to 25, 2 to 10, 2 to 5, 4 to 20, 5 to 25, 10 to 50, 25 to 75, 3 to 6, 5 to 15 termini). In some embodiments, a polymer is linear and therefore has 2 termini. In some embodiments, only one termini of a polymer backbone is covalently bonded to the structure of formula (1). In some embodiments, wherein a polymer has two termini, both termini of the polymer backbone are covalently bonded to the structure of formula (1).

A polymer backbone can be, for example, poly(alkylene glycol), poly(oxyethylated polyol), poly(olefinic alcohol), poly(α-hydroxy acid), poly(vinyl alcohol), polyoxazoline, or a copolymer thereof. A polyalkylene glycol includes linear or branched polymeric polyether polyols. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da. For example, a polymer used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, a polymer backbone is a linear or branched poly(ethylene glycol).

In some embodiments, the poly(ethylene glycol) molecule is a linear polymer. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, E is oxygen. In some embodiments, E is sulfur.

In some embodiments, K is a linear or branched alkylene. For example, K can be selected from the group consisting of: methylene, ethylene, propylene, isopropylene, butylene, isobutylene, sec-butylene, tert-butylene, and hexylene. In some embodiments, K can be an alkyleneoxyalkylene or an oligomeric alkyleneoxyalkylene. For example, K can be a residue from diethylene glycol, triethylene glycol, tetraethylene glycol, or hexaethylene glycol. In some embodiments, K is selected from the group consisting of —(CH$_2$)$_n$— and —((CH$_2$)$_n$—O—(CH$_2$)$_m$)$_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G is a hydrophobic separation handle. For example, G can be a substituted or unsubstituted trityloxy group. In some embodiments, G is selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O.

In some embodiments, L is a linear or branched alkylene. For example, L can be selected from the group consisting of: methylene, ethylene, propylene, isopropylene, butylene, isobutylene, sec-butylene, tert-butylene, and hexylene. In some embodiments, L can be an alkyleneoxyalkylene or an oligomeric alkyleneoxyalkylene. For example, L can be a residue from diethylene glycol, triethylene glycol, tetraethylene glycol or hexaethylene glycol. In some embodiments, L is selected from the group consisting of —(CH$_2$)$_n$— and —((CH$_2$)$_n$—O—(CH$_2$)$_m$)$_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L is a substituted or unsubstituted arylene. For example, L can be a structure with the formula:

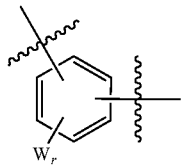

where W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —(CH$_2$)$_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NR$^9$C(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —SO$_2$, =S, —COOH, —NR$^9$$_2$, carbonyl, —C(O)—($C_1$-$C_{10}$ alkyl)-CF$_3$, —C(O)—CF$_3$, —C(O)NR$^9$$_2$, —($C_1$-$C_{10}$ aryl)-S—($C_6$-$C_{10}$ aryl), —C(O)—($C_6$-$C_{10}$ aryl), —(CH$_2$)$_m$—O—(CH$_2$)$_m$—O—($C_1$-$C_{10}$ alkyl) wherein each m is from 1 to 8, —C(O)NR$^9$$_2$, —C(S)NR$^9$$_2$, —SO$_2$NR$^9$$_2$, —NR$^9$C(O) NR$^9$$_2$, —NR$^9$C(S)NR$^9$$_2$, salts thereof, and the like. Each R$^9$ group in the preceding list independently includes, but is not limited to, H, alkyl or substituted alkyl, aryl or substituted aryl, or alkylaryl. In some embodiments, W is R$^1$ as described above.

Non-limiting examples of L include:

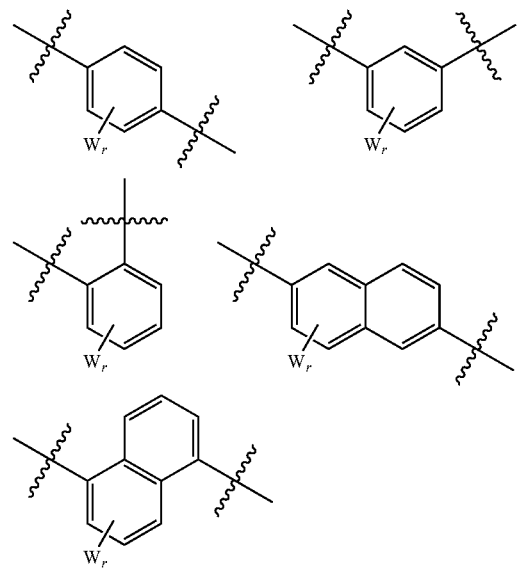

In some cases, L can also be a divalent radical of a nucleoside. For example, L can be a divalent radical of a natural nucleoside, such as adenosine, deoxyadenosine, guanosine, deoxyguanosine, 5-methyluridine, thymidine, uridine, deoxyuridine, cytidine, and deoxycytidine.

A group reactive with a biologically active molecule can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide. In some embodiments, the group is protected or further reacted with a group R as shown in the structure of formula (1). The point of attachment of such a group is well understood by those of skill in the art.

In some embodiments, M is a detectable functional group. A detectable functional group, as used herein, can be any chemical or substance which is used to provide a signal or contrast in imaging. The signal enhancing domain can be an organic molecule, metal ion, salt or chelate, particle (particularly iron particle), or labeled peptide, protein, polymer or liposome. For example, a detectable functional group can include one or more of a radionuclide, a paramagnetic metal, a fluorophore, a dye, and an enzyme substrate. In some embodiments, a detectable functional group is biotin or a fluorophore.

In some embodiments, the detectable functional group is a physiologically compatible metal chelate compound consisting of one or more cyclic or acyclic organic chelating agents complexed to one or more metal ions with atomic numbers 21-29, 42, 44, or 57-83.

For x-ray imaging, the detectable functional group may consist of iodinated organic molecules or chelates of heavy metal ions of atomic numbers 57 to 83. In some embodiments, the detectable functional group is $^{125}$I-IgG. Examples of suitable compounds are described in M. Sovak, ed., "Radiocontrast Agents," Springer-Verlag, pp. 23-125 (1984) and U.S. Pat. No. 4,647,447.

For ultrasound imaging, the detectable functional group can consist of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87. (1990).

For nuclear radiopharmaceutical imaging or radiotherapy, the detectable functional group can consist of a radioactive molecule. In some embodiments, the chelates of Tc, Re, Co, Cu, Au, Ag, Pb, Bi, In, and Ga can be used. In some embodiments, the chelates of Tc-99m can be used. Examples of suitable compounds are described in Rayudu G V S, *Radiotracers for Medical Applications*, I, pp. 201 and D. P. Swanson et al., ed., *Pharmaceuticals in Medical Imaging*, pp. 279-644 (1990).

For ultraviolet/visible/infrared light imaging, the detectable functional group can consist of any organic or inorganic dye or any metal chelate.

For MRI, the detectable functional group can consist of a metal-ligand complex of a paramagnetic form of a metal ion with atomic numbers 21-29, 42, 44, or 57-83. In some embodiments, the paramagnetic metal is chosen from: Gd(III), Fe(III), Mn(II and III), Cr(III), Cu(II), Dy(III), Tb(III), Ho(III), Er(III) and Eu(III). Many suitable chelating ligands for MRI agents are known in the art. These can also be used for metal chelates for other forms of biological imaging. For example, an imaging agent can include: Gadovist, Magnevist, Dotarem, Omniscan, and ProHance.

In some embodiments, R is absent. In some embodiments, R is a protecting group. For this purpose, R may include any suitable protecting group based on the group to be protected. For example, R may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2,2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-s dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3' pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, $R^1$ is a hydrophobic separation handle.

A hydrophobic separation handle is as described herein. In some embodiments, the hydrophobic separation handle is also a protecting group as described herein. In some embodiments, at least one of R, $R^1$, and G is a hydrophobic separation handle. For example, only one of R, $R^1$, and G is a hydrophobic separation handle.

In some embodiments, only one of $R^1$, R and G is a hydrophobic separation handle (e.g., a trityl group) as provided herein. For example, if R is a hydrophobic separation handle, then $R^1$ is absent and G is hydrogen or an alkoxy. In some embodiments, R is absent or a protecting group, $R^1$ is a hydrophobic separation handle, and G is hydrogen or an alkoxy. In some embodiments, wherein more than one of R, $R^1$ and G is a hydrophobic separation handle, one of R, $R^1$ and G is more hydrophobic than the others (e.g., substantially more hydrophobic). In some embodiments, the hydrophobic separation handle is a substituted or unsubstituted trityl or trityloxy group. For example, only one of R, $R^1$ and G is a substituted or unsubstituted trityl or trityloxy group.

A compound as described above can be prepared, for example, by contacting a water-soluble, non-peptidic and non-nucleotidic polymer, in a water-free solvent (e.g., an organic solvent), with a reagent of formula (4):

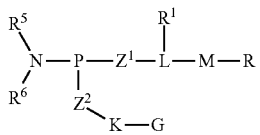

wherein:

$R^5$ and $R^6$ independently from each other represent $C_1$-$C_6$-alkyl or $R^5$ and $R^6$ jointly form a 5- or 6-membered ring with the N to which they are bonded. In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ can jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, or pyrazolyl, particularly 3- and 5-pyrazolyl. In some embodiments, $R^5$ and $R^6$ can jointly form a morpholine ring.

The ratio of a polymer to a reagent of formula (4) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (4) is from about 1:1 to about 1:10, for example, about 2:1.

An activating reagent can then be added to the mixture of the polymer and the reagent of formula (4). An activating reagent can be any group suitable to initiate coupling of the polymer and the reagent of formula (4). Suitable activating reagents include, for example, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

An oxidizing agent can then be added to oxidize $P^{+3}$ to $P^{+5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxides, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS), or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R is a protecting group or a hydrophobic separation handle and the method can include purifying the compound using chromatography (e.g., reverse phase chromatography). In some embodiments, the method also includes removing the protecting group.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and/or pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as described elsewhere by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some cases, a compound as described above can be further purified using precipitation and/or crystallization.

Compounds of Formula (2)

Also provided herein are compounds of formula (2):

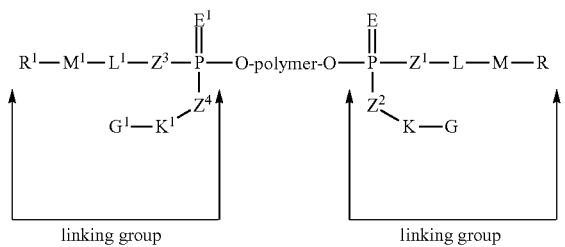

or a salt form thereof,
wherein:
polymer is a linear, water-soluble, non-peptidic, and non-nucleotidic polymer backbone, wherein each linking group is bonded at a different terminus of said polymer;
E and $E^1$ are independently O or S;
K and $K_1$ are independently selected from the group consisting of: alkylene, alkyleneoxyalkylene, and oligomeric alkyleneoxyalkylene;
G and $G_1$ are independently absent or are selected from the group consisting of: alkoxy and a hydrophobic separation handle;
each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH;
L and $L^1$ are independently selected from the group consisting of: a divalent radical of a nucleoside, alkylene, alkyleneoxyalkylene, oligomeric alkyleneoxyalkylene, and unsubstituted and substituted arylene;
M and $M^1$ are independently selected from a protected group that when deprotected is reactive with a biologically active molecule, a group reactive with a biologically active molecule, or is a detectable functional group, wherein M and $M^1$ are different; and
R and $R^1$ are independently absent, hydrogen, a protecting group, or an activating group;
wherein when M is a protected group that when deprotected is reactive with a biologically active molecule, then R is a protecting group or a hydrophobic separation handle;
wherein when M is a group reactive with a biologically active molecule, R is absent, hydrogen, or an activating group;
wherein when M is a detectable functional group, R is absent or hydrogen;
wherein when $M^1$ is a protected group that when deprotected is reactive with a biologically active molecule, then $R^1$ is a protecting group or a hydrophobic separation handle;
wherein when $M^1$ is a group reactive with a biologically active molecule, $R^1$ is absent, hydrogen, or an activating group; and
wherein when $M^1$ is a detectable functional group, $R^1$ is absent or hydrogen.

A polymer can be, for example, poly(alkylene glycol), poly(oxyethylated polyol), poly(olefinic alcohol), poly(α-hydroxy acid), poly(vinyl alcohol), polyoxazoline, or a copolymer thereof. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, the polymer is a poly(ethylene glycol) polymer. The molecular weight of the PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the PEG is between about 1,000 Da and about 50,000 Da. In some embodiments, the molecular weight of the n PEG is between about 1,000 Da and about 40,000 Da. In some embodiments, the molecular weight of the PEG is between about 5,000 Da and about 40,000 Da. In some embodiments, the molecular weight of the PEG is between about 5,000 Da and about 20,000 Da.

In some embodiments, $E^1$ is oxygen. In some embodiments, $E^1$ is sulfur. In some embodiments, $E^2$ is oxygen. In some embodiments, $E^2$ is sulfur. In some embodiments, both of $E^1$ and $E^2$ are oxygen.

In some embodiments, K and $K^1$ are independently selected from a linear or branched alkylene. For example, K and $K^1$ can be independently selected from the group consisting of: methylene, ethylene, propylene, isopropylene, butylene, isobutylene, sec-butylene, tert-butylene, and hexylene. In some embodiments, K and $K^1$ are independently an alkyleneoxyalkylene or an oligomeric alkyleneoxyalkylene. For example, K and $K^1$ can be independently a residue from diethylene glycol, triethylene glycol, tetraethylene glycol or hexaethylene glycol. In some embodiments, K and $K^1$ are independently selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G and $G^1$ are independently a hydrophobic separation handle. For example, G and $G^1$ are independently a substituted or unsubstituted trityloxy group. In some embodiments, G and $G^1$ are independently selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O. In some embodiments, one of $Z^1$ and $Z^2$ is NH and the other is O. For example, $Z^3$ is O and $Z^4$ is NH; $Z^3$ is NH and $Z^4$ is O. In some embodiments, both $Z^3$ and $Z^4$ are O. In some embodiments, one of $Z^1$ and $Z^2$ and $Z^3$ and $Z^4$ is NH and the other is O. For example, $Z^1$ and $Z^3$ are O and $Z^2$ and $Z^4$ are NH; $Z^1$ and $Z^3$ are NH and $Z^2$ and $Z^4$O. In some embodiments, $Z^1$ and $Z^3$ are O and $Z^2$ and $Z^4$ are O.

In some embodiments, L and $L^1$ are independently selected from a linear or branched alkyl. For example, L and $L^1$ can be independently selected from the group consisting of: methylene, ethylene, propylene, isopropylene, butylene, isobutylene, sec-butylene, tert-butylene, and hexylene. In some embodiments, L and $L^1$ are independently an alkyleneoxyalkylene or an oligomeric alkyleneoxyalkylene. For example, L and $L^1$ can be independently a residue from diethylene glycol, triethylene glycol, tetraethylene glycol or hexaethylene glycol. In some embodiments, L and $L^1$ are independently selected from the group consisting of $-(CH_2)_n-$ and $-((CH_2)_n-O-(CH_2)_m)_p-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L and $L^1$ are independently a substituted or unsubstituted arylene. For example, L and $L^1$ can be independently a structure with the formula:

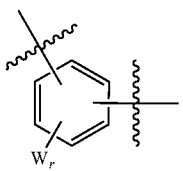

wherein W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, $-(CH_2)_m-O-(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, $-NO_2$, $-CN$, $-NR^9C(O)-(C_1$-$C_{10}$ alkyl), $-C(O)-(C_1$-$C_{10}$ alkyl), $C_2$-$C_{10}$ alkthioalkyl, $-C(O)O-(C_1$-$C_{10}$ alkyl), $-OH$, $-SO_2$, $=S$, $-COOH$, $-NR^9_2$, carbonyl, $-C(O)-(C_1$-$C_{10}$ alkyl)-$CF_3$, $-C(O)-CF_3$, $-(O)NR^9_2$, $-(C_1$-$C_{10}$ aryl)-S-($C_6$-$C_{10}$ aryl), $-C(O)-(C_6$-$C_{10}$ aryl), $-(CH_2)_m-O-(CH_2)_m-O-(C_1$-$C_{10}$ alkyl) wherein each m is from 1 to 8, $-C(O)NR^9_2$, $-C(S)NR^9_2$, $-SO_2NR^9_2$, $-NR^9C(O)NR^9_2$, $-NR^9C(S)NR^9_2$, salts thereof, and the like. Each $R^9$ group in the preceding list independently includes, but is not limited to, H, alkyl or substituted alkyl, aryl or substituted aryl, or alkylaryl. In some embodiments, W is $R^1$ as described above.

Non-limiting examples of L and $L^1$ include:

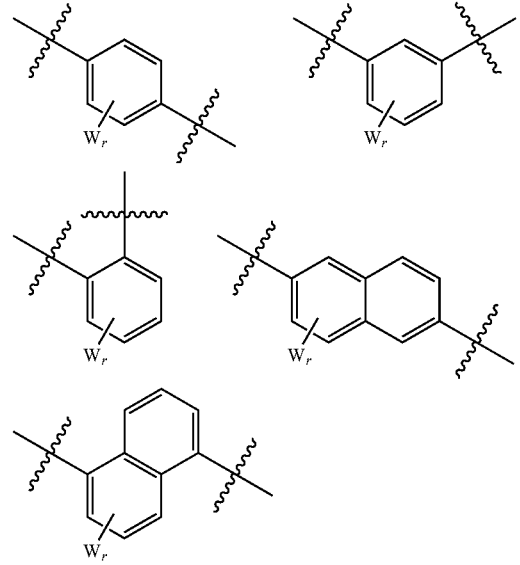

L and $L^1$ can also independently be a divalent radical of a nucleoside. For example, L and $L^1$ can be a divalent radical of a natural nucleoside, such as adenosine, deoxyadenosine, guanosine, deoxyguanosine, 5-methyluridine, thymidine, uridine, deoxyuridine, cytidine, and deoxycytidine.

A group reactive with a biologically active molecule can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide. In some embodiments, the group is protected or further reacted with a group R and $R^1$ as shown in the formula (2). The point of attachment of such a group is well understood by those of skill in the art.

In some embodiments, M and/or $M^1$ is a detectable functional group. A detectable functional group, as used herein, can be any chemical or substance which is used to provide a signal or contrast in imaging. The signal enhancing domain can be an organic molecule, metal ion, salt or chelate, particle (particularly iron particle), or labeled peptide, protein, polymer or liposome. For example, a detectable functional group can include one or more of a radionuclide, a paramagnetic metal, a fluorophore, a dye, and an enzyme substrate. In some embodiments, a detectable functional group is biotin or a fluorophore.

In some embodiments, the detectable functional group is a physiologically compatible metal chelate compound consisting of one or more cyclic or acyclic organic chelating agents complexed to one or more metal ions with atomic numbers 21-29, 42, 44, or 57-83.

For x-ray imaging, the detectable functional group may consist of iodinated organic molecules or chelates of heavy metal ions of atomic numbers 57 to 83. In some embodiments, the detectable functional group is $^{125}$I-IgG. Examples of suitable compounds are described in M. Sovak, ed., "Radiocontrast Agents," Springer-Verlag, pp. 23-125 (1984) and U.S. Pat. No. 4,647,447.

For ultrasound imaging, the detectable functional group can consist of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87. (1990).

For nuclear radiopharmaceutical imaging or radiotherapy, the detectable functional group can consist of a radioactive molecule. In some embodiments, the chelates of Tc, Re, Co, Cu, Au, Ag, Pb, Bi, In, and Ga can be used. In some embodiments, the chelates of Tc-99m can be used. Examples of suitable compounds are described in Rayudu G V S, *Radiotracers for Medical Applications*, I, pp. 201 and D. P. Swanson et al., ed., *Pharmaceuticals in Medical Imaging*, pp. 279-644 (1990).

For ultraviolet/visible/infrared light imaging, the detectable functional group can consist of any organic or inorganic dye or any metal chelate.

For MRI, the detectable functional group can consist of a metal-ligand complex of a paramagnetic form of a metal ion with atomic numbers 21-29, 42, 44, or 57-83. In some embodiments, the paramagnetic metal is chosen from: Gd(III), Fe(III), Mn(II and III), Cr(III), Cu(II), Dy(III), Tb(III), Ho(III), Er(III) and Eu(III). Many suitable chelating ligands for MRI agents are known in the art. These can also be used for metal chelates for other forms of biological imaging. For example, an imaging agent can include: Gadovist, Magnevist, Dotarem, Omniscan, and ProHance.

In some embodiments, R and/or $R^1$ is absent. In some embodiments, R and/or $R^1$ is a protecting group. For this purpose, R and/or $R^1$ may include any suitable protecting group based on the group to be protected. For example, R and/or $R^1$ may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2, 2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N, N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3' pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, R and/or $R^1$ is a hydrophobic separation handle.

A hydrophobic separation handle is as described herein. In some embodiments, the hydrophobic separation handle is also a protecting group as described herein. In some embodiments, at least one of R, $R^1$, G, and $G^1$ is a hydrophobic separation handle.

In some embodiments, only one of R and G and $R^1$ and $G^1$ is a hydrophobic separation handle (e.g., a trityl group) as provided herein. For example, if R is a hydrophobic separation handle, then G is hydrogen or an alkoxy. Alternatively, if $R^1$ is a hydrophobic separation handle, then $G^1$ is absent or an alkoxy. In some embodiments, R is absent or a protecting group, $R^1$ is a hydrophobic separation handle, and G and $G^1$ are independently absent or an alkoxy, wherein $R^1$ is more hydrophobic than R. In some embodiments, $R^1$ is absent or a protecting group, R is a hydrophobic separation handle, and G and $G^1$ are independently absent or an alkoxy, wherein R is more hydrophobic than $R^1$. In some embodiments, the hydrophobic separation handle is a substituted or unsubstituted trityl or trityloxy group. For example, only one of R, $R^1$, G, and $G^1$ is a substituted or unsubstituted trityl or trityloxy group.

A compound as described above can be prepared, for example, by contacting a water-soluble, non-peptidic and non-nucleotidic polymer, in a water-free solvent (e.g., an organic solvent), with a reagent selected from formula (5):

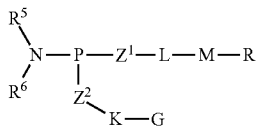

wherein:
$R^5$ and $R^6$ independently from each other represent $C_1$-$C_6$-alkyl or $R^5$ and $R^6$ jointly form a 5- or 6-membered ring with the N to which they are bonded, and formula (6):

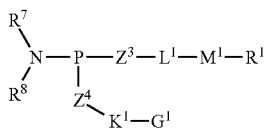

wherein:
$R^7$ and $R^8$ independently from each other represent $C_1$-$C_6$-alkyl or $R^7$ and $R^8$ jointly form a 5- or 6-membered ring with the N to which they are bonded;
under conditions that facilitate formation of monoderivatized product.

In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^5$ and $R^6$ jointly form a morpholine ring.

In some embodiments, $R^7$ and $R^8$ are independently a $C_1$-$C_6$-alkyl. For example, $R^7$ and $R^8$ can be independently selected from the group consisting of methyl, ethyl, propyl, isopropyl, butyl, isobutyl, sec-butyl, tert-butyl, and hexyl. In some embodiments, $R^7$ and $R^8$ are isopropyl. In some embodiments, $R^7$ and $R^8$ jointly form a 5- or 6-membered ring with the N to which they are bonded. For example, $R^7$ and $R^8$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^7$ and $R^8$ jointly form a morpholine ring.

The ratio of a polymer to a reagent of formula (5) or (6) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (5) or (6) is from about 1:1 to about 1:10. In some embodiments, the ratio of a polymer to a reagent of formula (5) or (6) is about 2:1.

In some embodiments, conditions that facilitate formation of a monoderivatized product include the addition of an activating reagent. An activating reagent is then added to the mixture of the polymer and the reagent of formula (4) or (5). An activating reagent can be any group suitable to initiate coupling of the polymer and the reagent of formula (4). Suitable activating reagents include, for example, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

In some embodiments, conditions that facilitate formation of a monoderivatized product include addition of an oxidizing agent to oxidize $P^{+3}$ to $P^{+5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography).

To the monoderivatized product, a reagent of formula (4) or formula (5) is added under conditions that facilitate the conversion of the monoderivatized product to a compound of formula (2). In some embodiments, the reagent is different from the reagent used to prepare the monoderivatized product. In some embodiments, the reagent is the same as that used to prepare the monoderivatized product.

In some embodiments, the conditions are such that conversion of the monoderivatized product to the compound of formula (2) is quantitative.

In some embodiments, conditions that facilitate formation of a compound of formula (2) include the addition of an activating reagent. An activating reagent is then added to the mixture of the monoderivatized product and the reagent of formula (5) or (6). An activating reagent can be any group suitable to initiate coupling of the polymer and the reagent of formula (5) or (6). Suitable activating reagents include, for example, 1H-tetrazole, 5-(ethylthio)-1H-tetrazole (ETT), 5-(benzylthio)-1H-tetrazole (BTT), Activator 42 (5-(3,5-bis (trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

In some embodiments, conditions that facilitate formation of a compound of formula (2) include addition of an oxidizing agent to oxidize $P^{+3}$ to $P^{+5}$. Suitable oxidizing agents and conditions can be readily determined by those of ordinary skill in the art. For example, an oxidant such as $RuO_4^-/NMO$, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography). In some embodiments, the method further includes removal of one or more of the protecting groups. In some embodiments, the method further includes removal of one or more of the hydrophobic separation handles.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as reported by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some embodiments, the method can also include isolating the compound by precipitation or crystallization.

Compounds of Formula (3)

Also provided herein is a compound of formula (3):

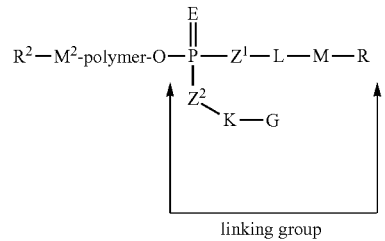

linking group or a salt form thereof,
wherein:
polymer is a linear, water-soluble, non-peptidic, and non-nucleotidic polymer backbone, wherein $M^2$ and the phosphonate-derived functional group are bonded at a different terminus of said polymer;
E and $E^1$ are independently O or S;
K is selected from the group consisting of: alkylene, alkyleneoxyalkylene, and oligomeric alkyleneoxyalkylene;
G is selected from the group consisting of hydrogen, alkoxy and a hydrophobic separation handle;
$Z^1$ and $Z^2$ are independently selected from O and NH, wherein only one of $Z^1$ and $Z^2$ can be NH;
L is selected from the group consisting of: a divalent radical of a nucleoside, alkylene, alkyleneoxyalkylene, oligomeric alkyleneoxyalkylene, and unsubstituted and substituted arylene;
M is selected from a protected group that when deprotected is reactive with a biologically active molecule, a group reactive with a biologically active molecule, or is a detectable functional group;
$M^2$ is selected from O, S or NH; and
R is absent, a protecting group, a hydrophobic separation handle, or an activating group;
$R^2$ is hydrogen or a protecting group;
wherein when M is a protected group that when deprotected is reactive with a biologically active molecule, then R is a protecting group or a hydrophobic separation handle;
wherein when M is a group reactive with a biologically active molecule, R is absent, hydrogen, or an activating group; and wherein when M is a detectable functional group, R is absent or hydrogen.

A polymer can be, for example, poly(alkylene glycol), poly(oxyethylated polyol), poly(olefinic alcohol), poly(α-hydroxy acid), poly(vinyl alcohol), polyoxazoline, or a copolymer thereof. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, the polymer is a poly(ethylene glycol) polymer. The molecular weight of the PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the PEG is between about 1,000 Da and about 50,000 Da. In some embodiments, the molecular weight of the n PEG is between about 1,000 Da and about 40,000 Da. In some embodiments, the molecular weight of the PEG is between about 5,000 Da and about 40,000 Da. In some embodiments, the molecular weight of the PEG is between about 5,000 Da and about 20,000 Da.

In some embodiments, E is oxygen. In some embodiments, E is sulfur.

In some embodiments, K is a linear or branched alkylene. For example, K can be selected from the group consisting of: methylene, ethylene, propylene, isopropylene, butylene, isobutylene, sec-butylene, tert-butylene, and hexylene. In some embodiments, K can be an alkyleneoxyalkylene or an oligomeric alkyleneoxyalkylene. For example, K can be a residue from diethylene glycol, triethylene glycol, tetraethylene glycol or hexaethylene glycol. In some embodiments, K is selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G is a hydrophobic separation handle. For example, G can be a substituted or unsubstituted trityloxy group. In some embodiments, G is selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O.

In some embodiments, L is a linear or branched alkyl. For example, L can be selected from the group consisting of: methylene, ethylene, propylene, isopropylene, butylene, isobutylene, sec-butylene, tert-butylene, and hexylene. In some embodiments, L can be an alkyleneoxyalkylene or an oligomeric alkyleneoxyalkylene. For example, L can be a residue from diethylene glycol, triethylene glycol, tetraethylene glycol or hexaethylene glycol. In some embodiments, L is selected from the group consisting of —$(CH_2)_n$— and —$((CH_2)$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L is a substituted or unsubstituted arylene. For example, L can be a structure with the formula:

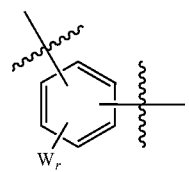

wherein W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—$(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —$NR^9C(O)$—$(C_1$-$C_{10}$ alkyl), —$C(O)$—$(C_1$-$C_{10}$ alkyl), $C_2$-$C_{10}$ alkthioalkyl, —$C(O)O$—$(C_1$-$C_{10}$ alkyl), —OH, —$SO_2$, =S, —COOH, —$NR^9{}_2$, carbonyl, —$C(O)$—$(C_1$-$C_{10}$ alkyl)-$CF_3$, —$C(O)$—$CF_3$, —$C(O)NR^9{}_2$, —$(C_1$-$C_{10}$ aryl)-S—$(C_6$-$C_{10}$ aryl), —$C(O)$—$(C_6$-$C_{10}$ aryl), —$(CH_2)_m$—O—$(CH_2)_m$—O—$(C_1$-$C_{10}$ alkyl) wherein each m is from 1 to 8, —$C(O)NR^9{}_2$, —$C(S)NR^9{}_2$, —$SO_2NR^9{}_2$, —$NR^9C(O)NR^9{}_2$, —$NR^9C(S)NR^9{}_2$, salts thereof, and the like. Each $R^9$ group in the preceding list independently includes, but is not limited to, H, alkyl or substituted alkyl, aryl or substituted aryl, or alkylaryl. In some embodiments, W is $R^1$ as described above.

Non-limiting examples of L include:

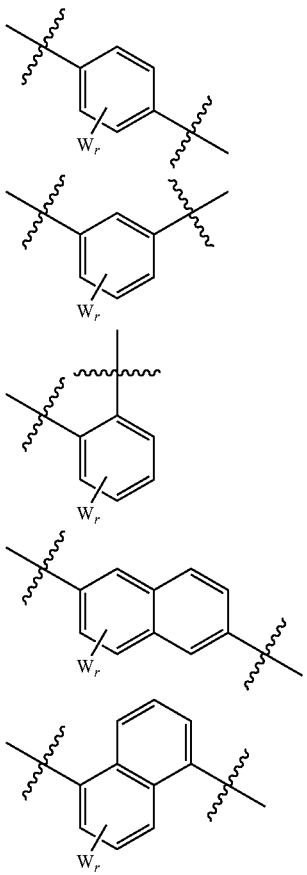

L can also be a divalent radical of a nucleoside. For example, L can be a divalent radical of a natural nucleoside, such as adenosine, deoxyadenosine, guanosine, deoxyguanosine, 5-methyluridine, thymidine, uridine, deoxyuridine, cytidine, and deoxycytidine.

A group reactive with a biologically active molecule can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide. In some embodiments, the group is protected or further reacted with a group R as shown in the structure of formula (3). The point of attachment of such a group is well understood by those of skill in the art.

In some embodiments, M is a detectable functional group. A detectable functional group, as used herein, can be any chemical or substance which is used to provide a signal or contrast in imaging. The signal enhancing domain can be an organic molecule, metal ion, salt or chelate, particle (particularly iron particle), or labeled peptide, protein, polymer or liposome. For example, a detectable functional group can include one or more of a radionuclide, a paramagnetic metal, a fluorophore, a dye, and an enzyme substrate. In some embodiments, a detectable functional group is biotin or a fluorophore.

In some embodiments, the detectable functional group is a physiologically compatible metal chelate compound consisting of one or more cyclic or acyclic organic chelating agents complexed to one or more metal ions with atomic numbers 21-29, 42, 44, or 57-83.

For x-ray imaging, the detectable functional group may consist of iodinated organic molecules or chelates of heavy metal ions of atomic numbers 57 to 83. In some embodiments, the detectable functional group is $^{125}$I-IgG. Examples of suitable compounds are described in M. Sovak, ed., "Radiocontrast Agents," Springer-Verlag, pp. 23-125 (1984) and U.S. Pat. No. 4,647,447.

For ultrasound imaging, the detectable functional group can consist of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging, pp.* 682-87. (1990).

For nuclear radiopharmaceutical imaging or radiotherapy, the detectable functional group can consist of a radioactive molecule. In some embodiments, the chelates of Tc, Re, Co, Cu, Au, Ag, Pb, Bi, In, and Ga can be used. In some embodiments, the chelates of Tc-99m can be used. Examples of suitable compounds are described in Rayudu G V S, *Radiotracers for Medical Applications*, I, pp. 201 and D. P. Swanson et al., ed., *Pharmaceuticals in Medical Imaging, pp.* 279-644 (1990).

For ultraviolet/visible/infrared light imaging, the detectable functional group can consist of any organic or inorganic dye or any metal chelate.

For MRI, the detectable functional group can consist of a metal-ligand complex of a paramagnetic form of a metal ion with atomic numbers 21-29, 42, 44, or 57-83. In some embodiments, the paramagnetic metal is chosen from: Gd(III), Fe(III), Mn(II and III), Cr(III), Cu(II), Dy(III), Tb(III), Ho(III), Er(III) and Eu(III). Many suitable chelating ligands for MRI agents are known in the art. These can also be used for metal chelates for other forms of biological imaging. For example, an imaging agent can include: Gadovist, Magnevist, Dotarem, Omniscan, and ProHance.

In some embodiments, R is absent.

In some embodiments, $R^2$ is hydrogen.

In some embodiments, R and/or $R^2$ is a protecting group. For this purpose, R and/or $R^2$ may include any suitable protecting group based on the group to be protected. For example, R and/or $R^2$ may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2,2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N, N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3' pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide, 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, R is a hydrophobic separation handle.

A hydrophobic separation handle is as described herein. In some embodiments, the hydrophobic separation handle is also a protecting group as described herein. In some embodiments, at least one of R and G is a hydrophobic separation handle.

In some embodiments, only one of R and G is a hydrophobic separation handle (e.g., a trityl group) as provided herein. For example, if R is a hydrophobic separation handle, then G is hydrogen or an alkoxy. In some embodiments, R is a protecting group and G is hydrogen or an alkoxy. In some embodiments, R is absent and G is a trityloxy group. In some embodiments, the hydrophobic separation handle is a substituted or unsubstituted trityl or trityloxy group. For example, only one of R and G is a substituted or unsubstituted trityl or trityloxy group.

In some embodiments, $R^2$ is absent or is selected from the group consisting of: trityl, monoalkoxytrityl, dialkoxytrityl, pixyl, alkoxypixyl, fluorenylmethyloxycarbonyl, alkylcarboxyl, benzoyl, tetrahydropyranyl, and methyl.

A compound of formula (3) can be prepared, for example, by contacting a monosubstituted polymer comprising a linear, water-soluble, non-peptidic and non-nucleotidic polymer backbone bonded at the first terminus with the functional group $M^2$-$R^2$, with a reagent of formula (5):

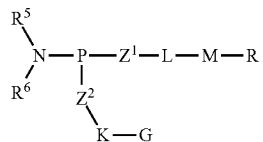

wherein:

$R^5$ and $R^6$ independently from each other represent $C_1$-$C_6$-alkyl or $R^5$ and $R^6$ jointly form a 5- or 6-membered ring with the N to which they are bonded; under conditions facilitating the conversion of the monosubstituted polymer to a compound of formula (3).

In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^5$ and $R^6$ jointly form a morpholine ring.

The ratio of a monosubstituted polymer to a reagent of formula (5) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (5) is from about 1:1 to about 1:10. In some embodiments, the ratio of a polymer to a reagent of formula (5) is about 2:1.

In some embodiments, the conversion of a monosubstituted polymer to a compound of formula (3) is quantitative.

In some embodiments, conditions that facilitate formation of a compound of formula (3) include the addition of an activating reagent. An activating reagent is then added to the mixture of the monoderivatized product and the reagent of formula (5) or (6). An activating reagent can be any group suitable to initiate coupling of the polymer and the reagent of formula (5) or (6). Suitable activating reagents include, for example, 1H-tetrazole, 5-(ethylthio)-1H-tetrazole (ETT), 5-(benzylthio)-1H-tetrazole (BTT), Activator 42 (5-(3,5-bis (trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

In some embodiments, conditions that facilitate formation of a compound of formula (3) include addition of an oxidizing agent to oxidize $P^{+3}$ to $P^{+5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography). In some embodiments, the method further includes removal of one or more of the protecting groups. In some embodiments, the method further includes removal of one or more of the hydrophobic separation handles.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as reported by R. M. Hann et al., *J. Am. Chem. Soc.,* 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "The Fluorenylmethoxycarbonyl Amino Protecting Group," in The Peptides, S. Udenfriend and J. Meienhofer, Academic Press, New York, 1987, p. 1. t-butyl carbamate (Boc) can be removed, as reported by G. L. Stahl et al., *J. Org. Chem.,* 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.,* 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some embodiments, the method can also include isolating the compound of formula (3) by precipitation or crystallization.

Non-limiting examples of linking groups for use in the compounds provided herein include:

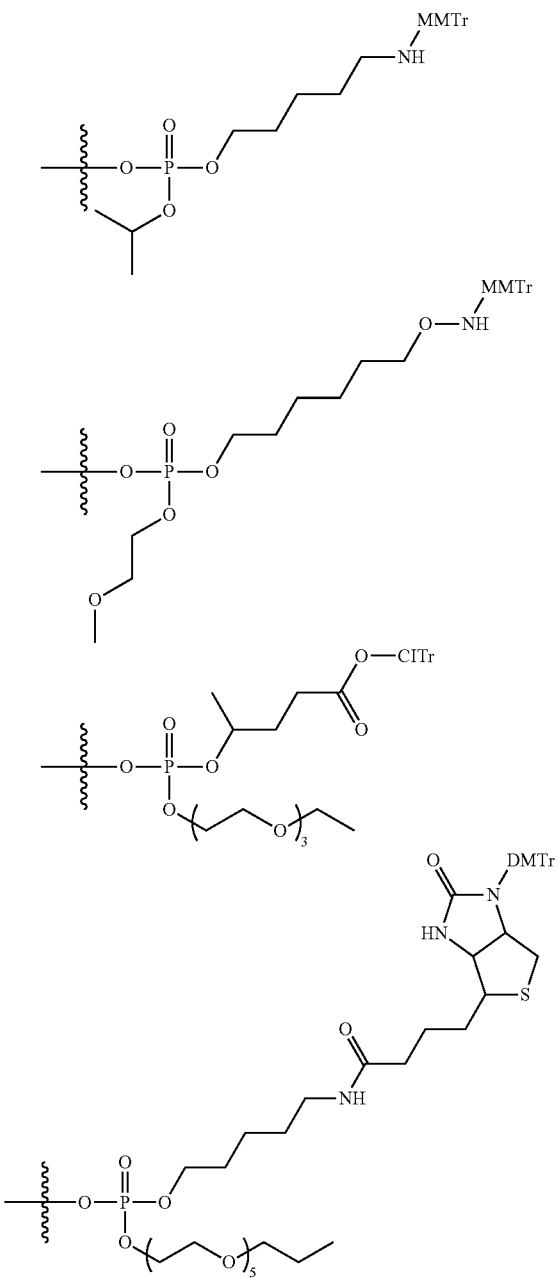

45
-continued
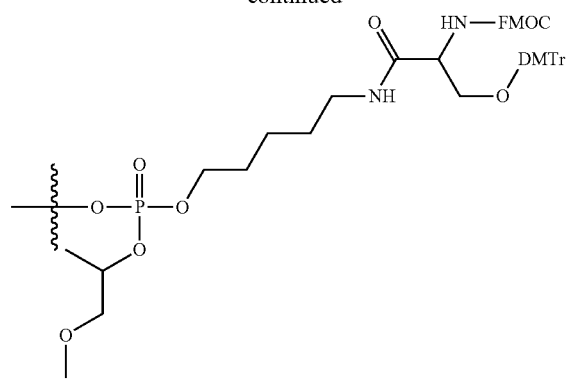
46
-continued
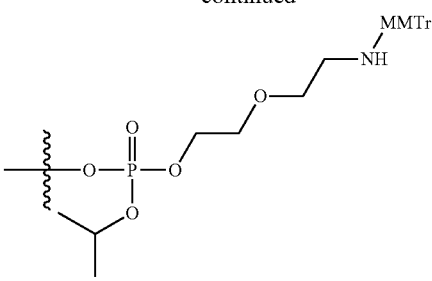
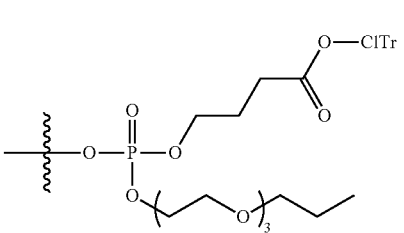
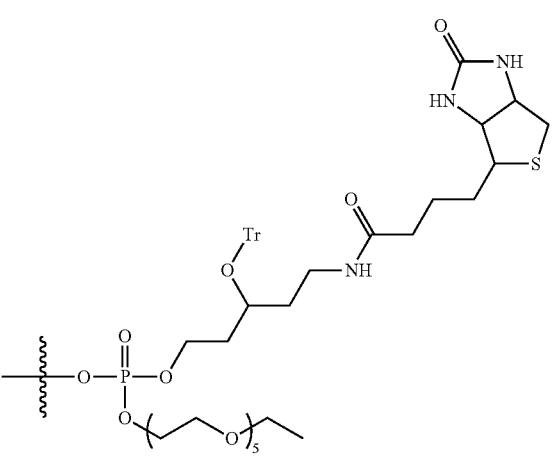
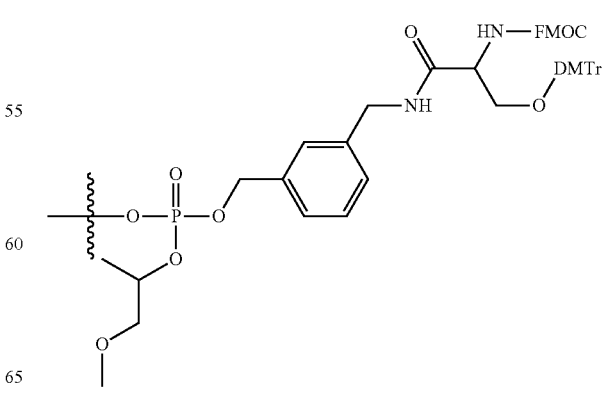

47
-continued
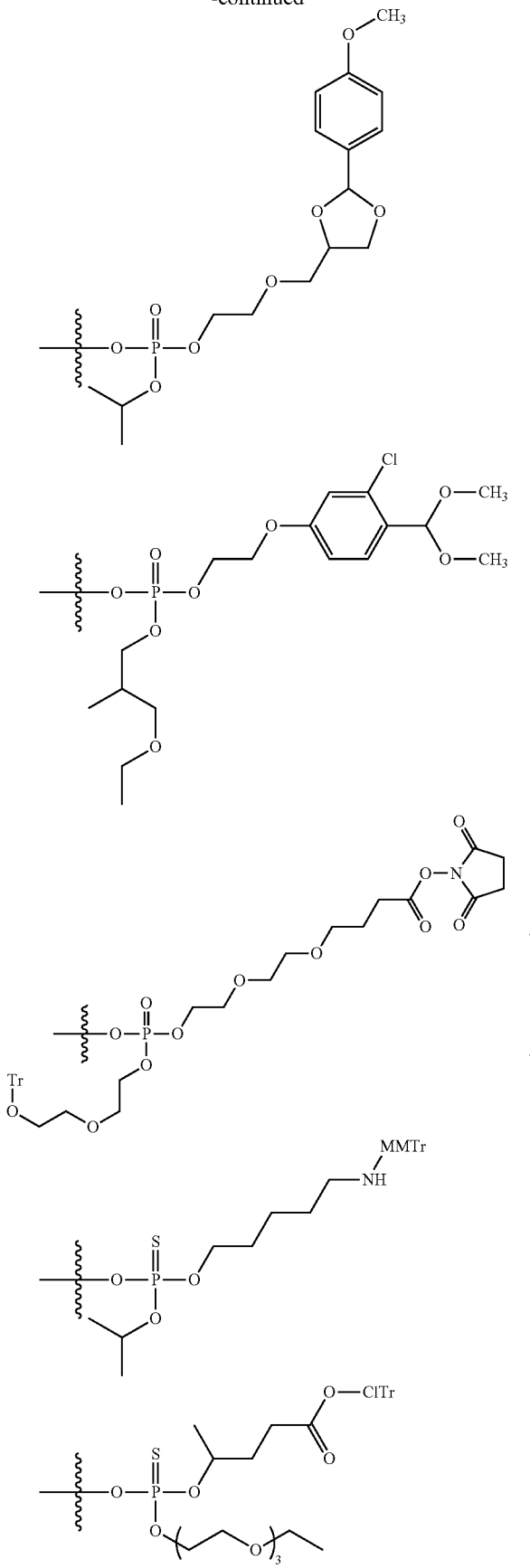
48
-continued
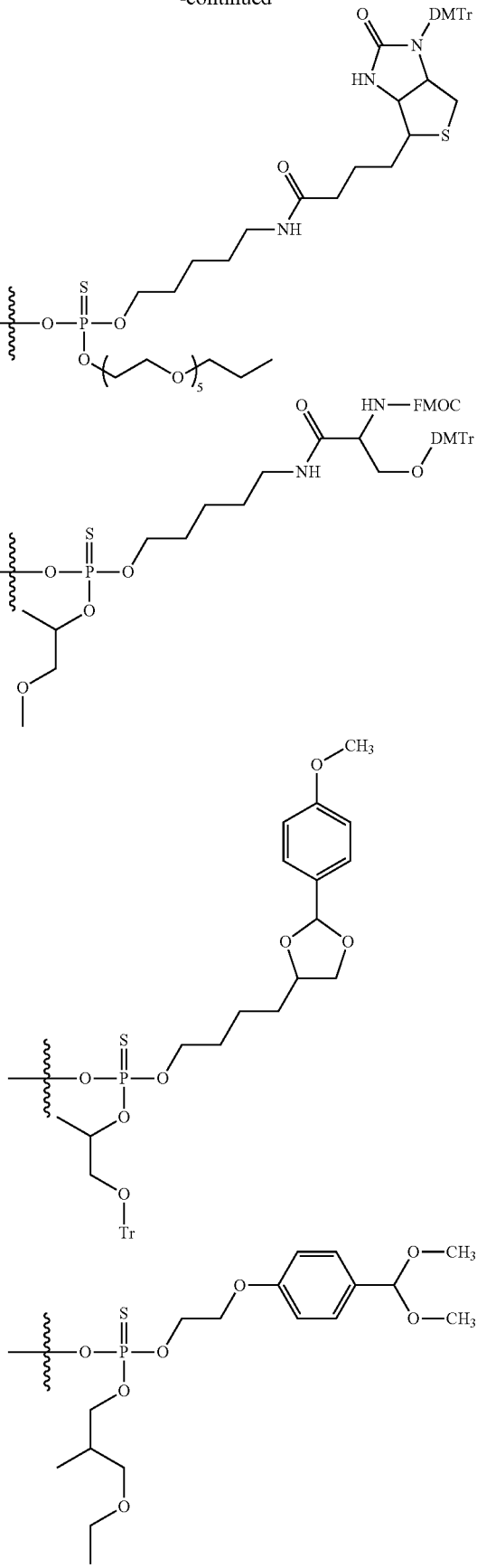

49
-continued
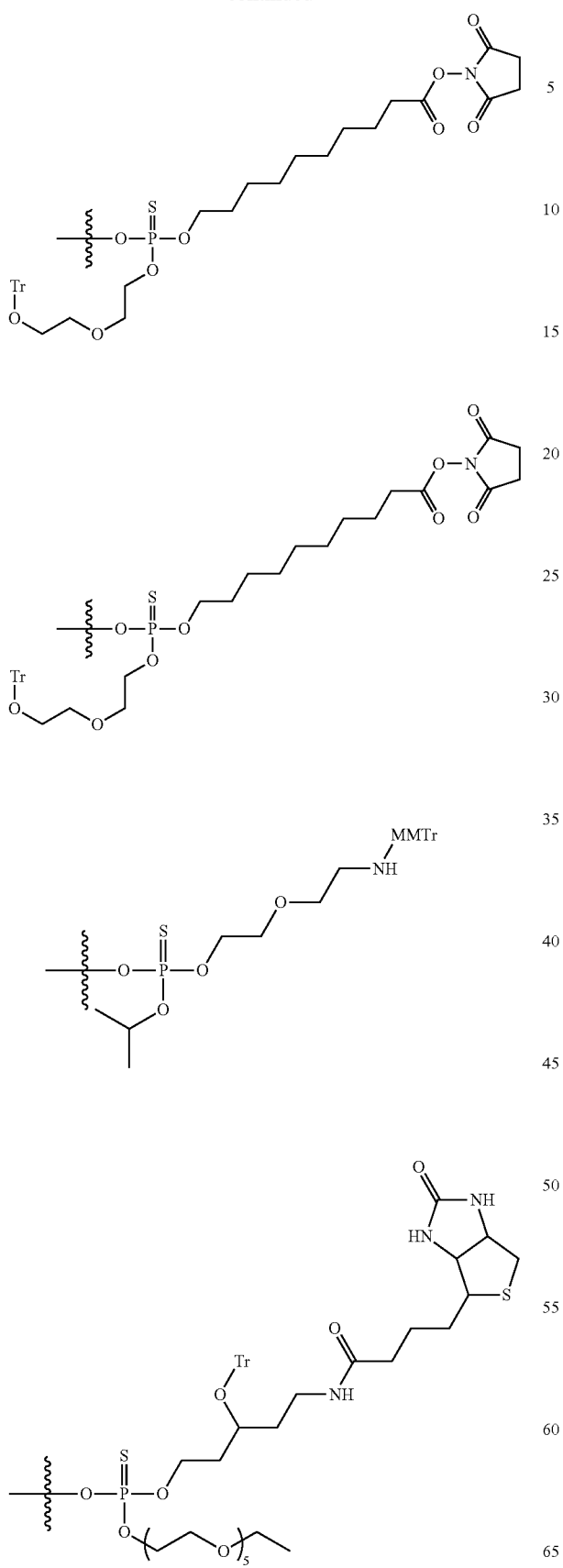
50
-continued
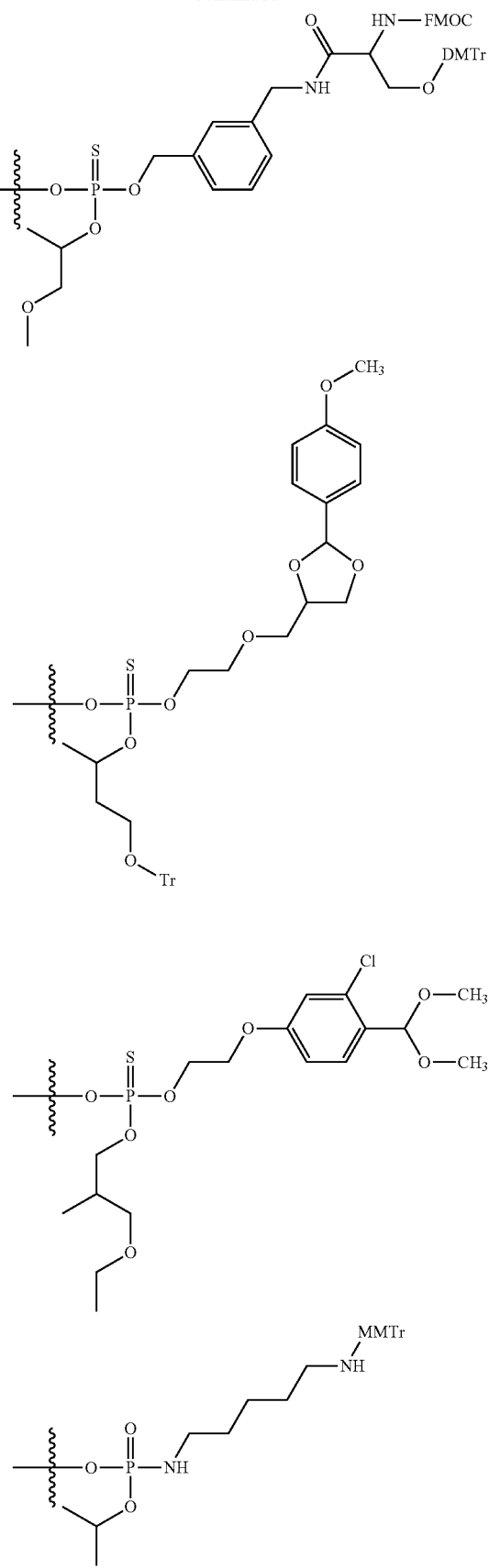

51
-continued
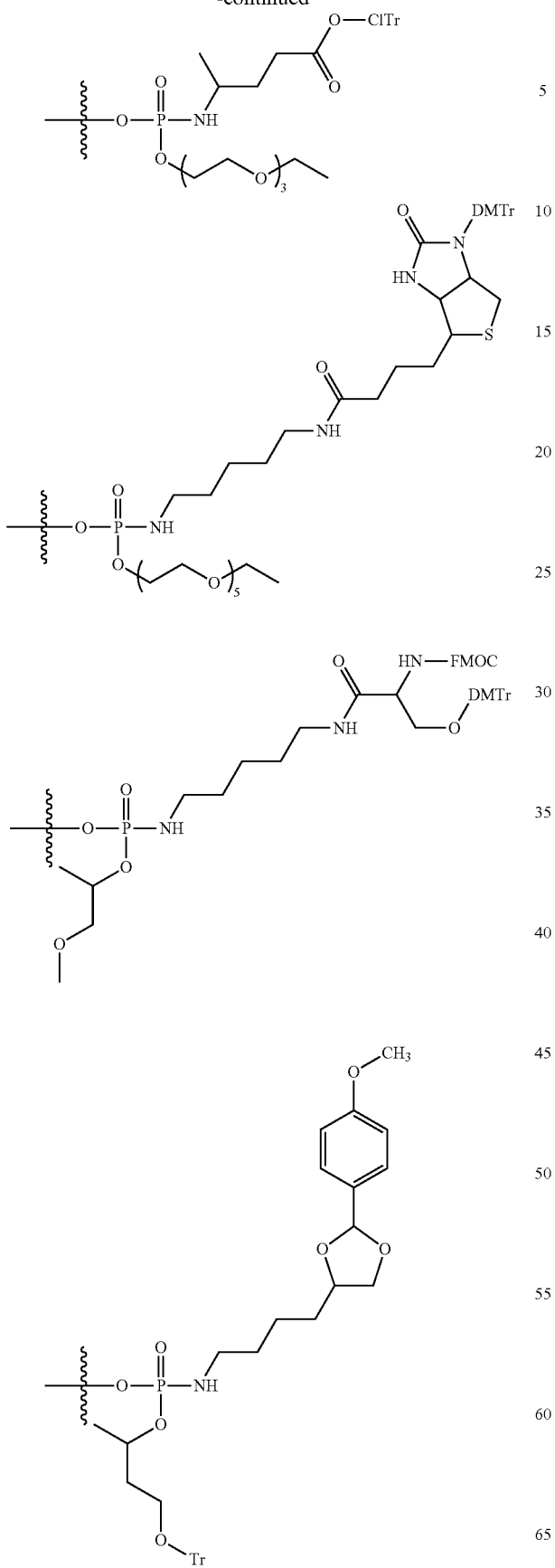
52
-continued
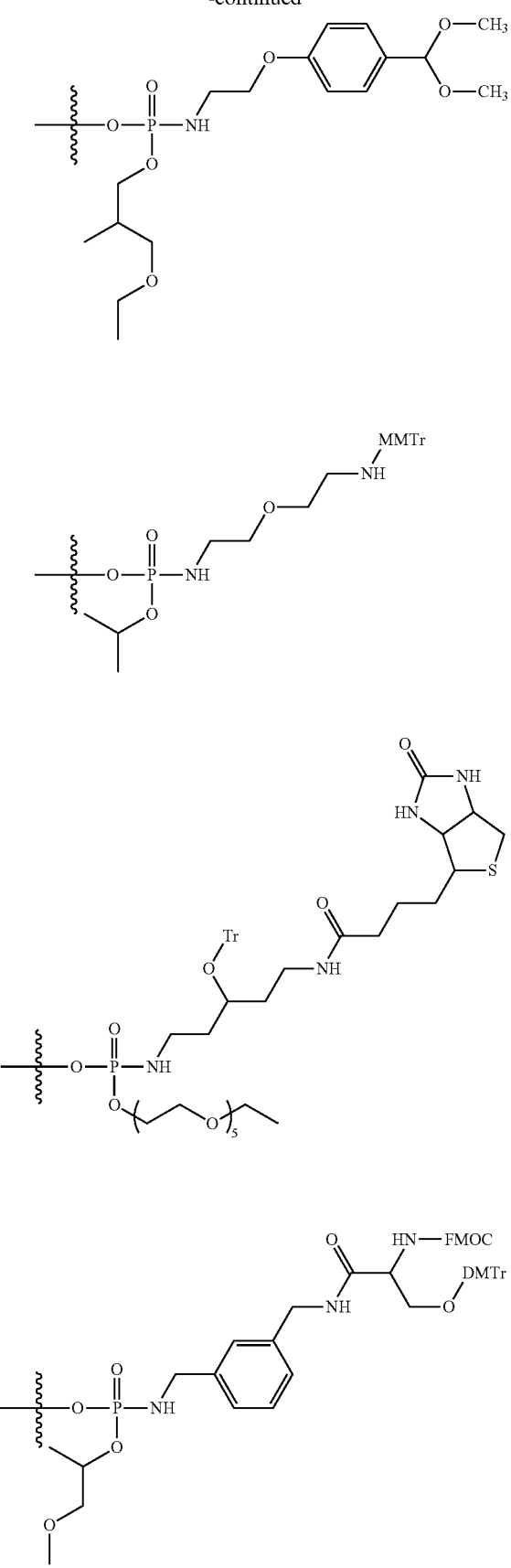

53
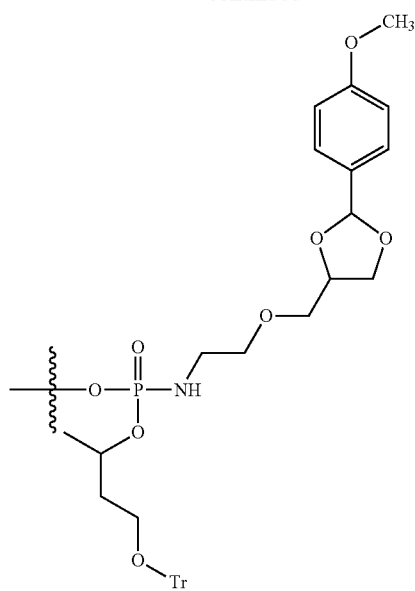
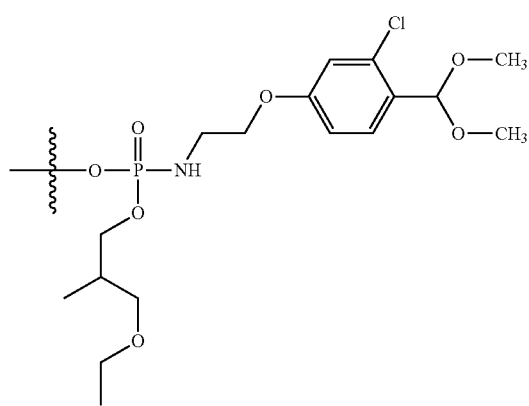
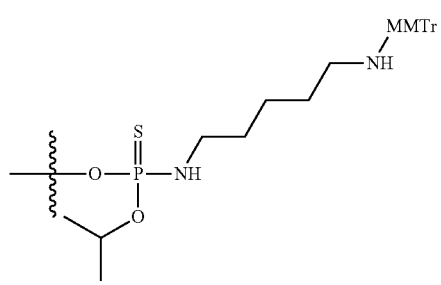
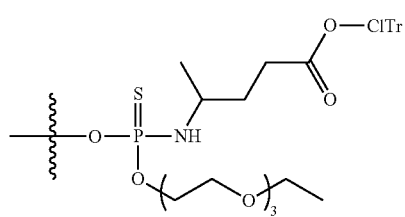
54
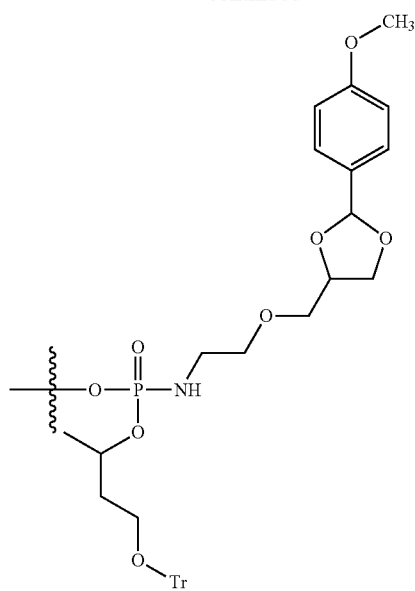
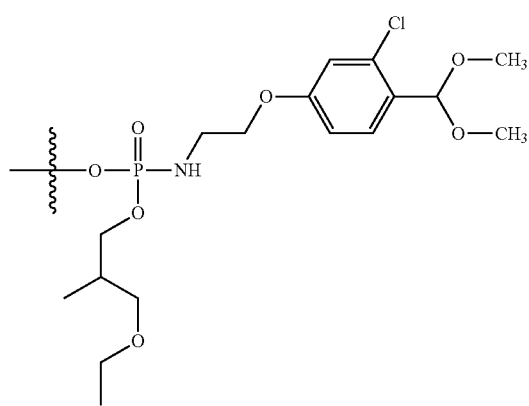
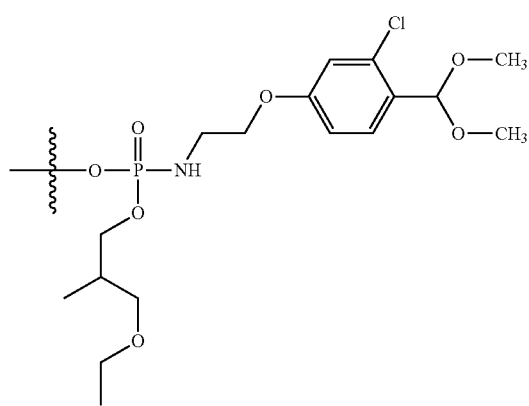

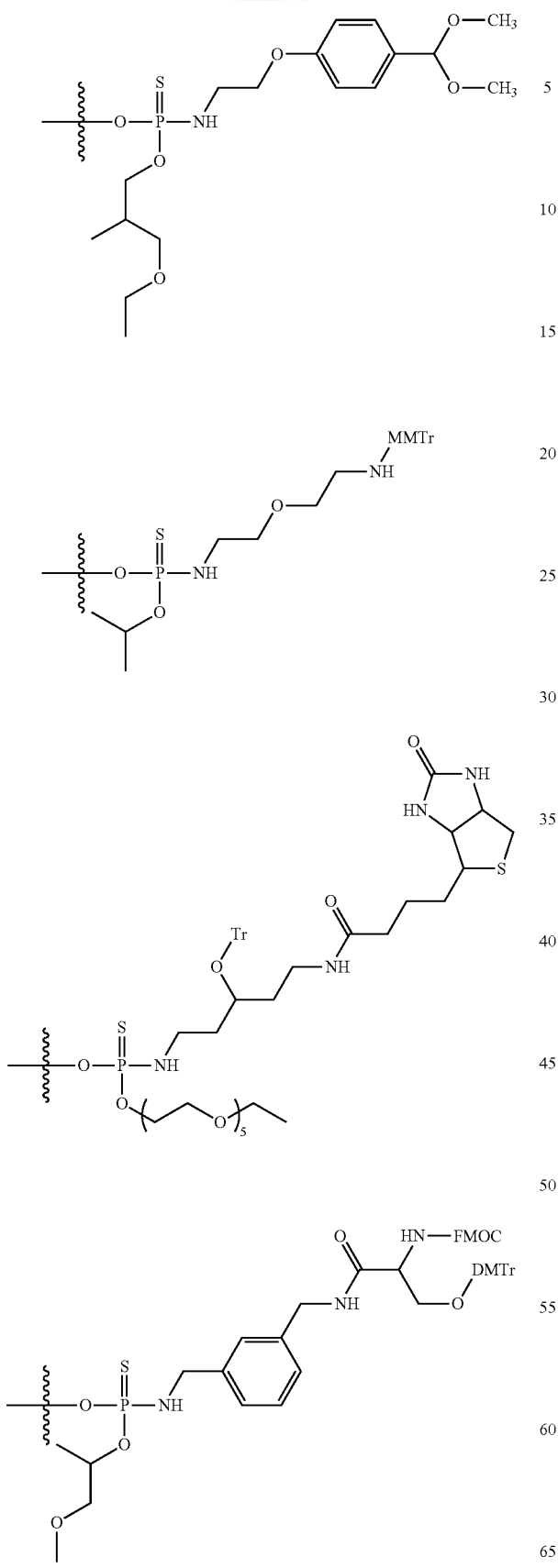
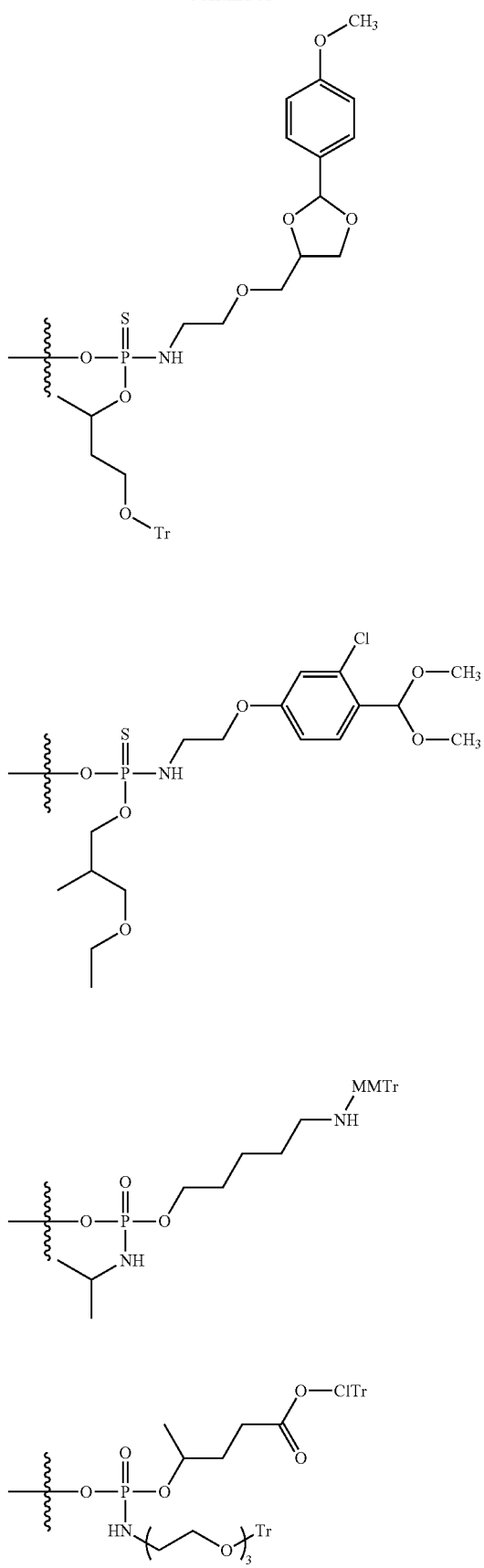

57
-continued
58
-continued
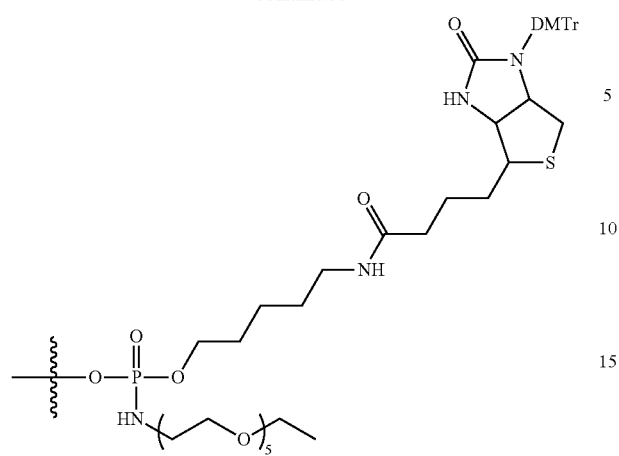
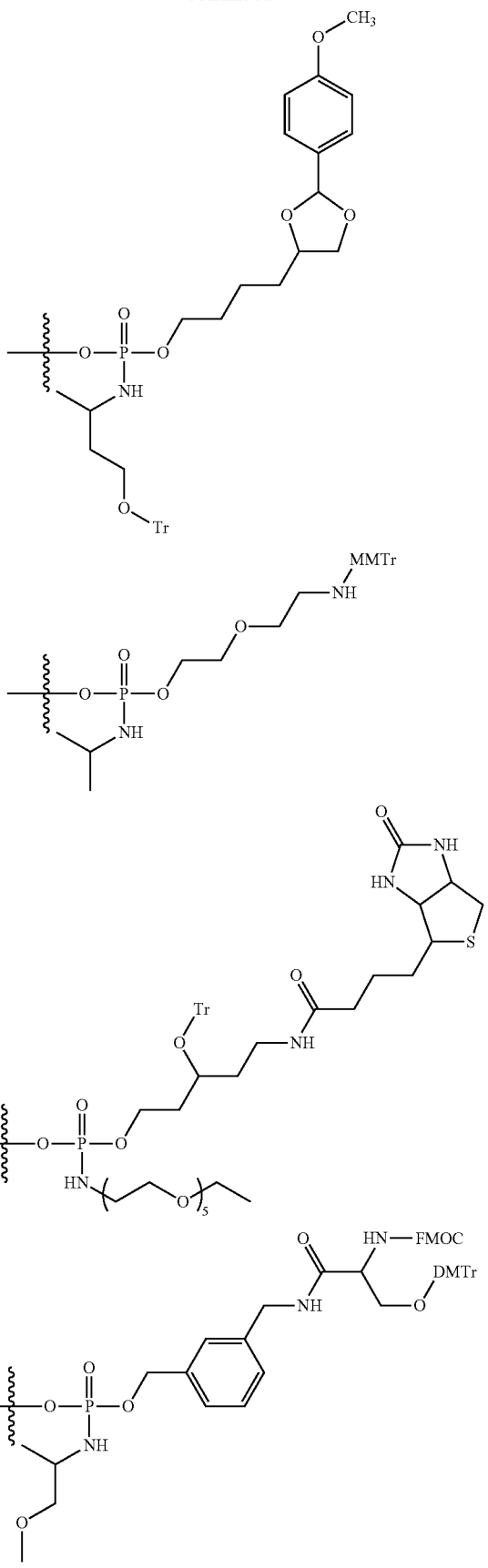

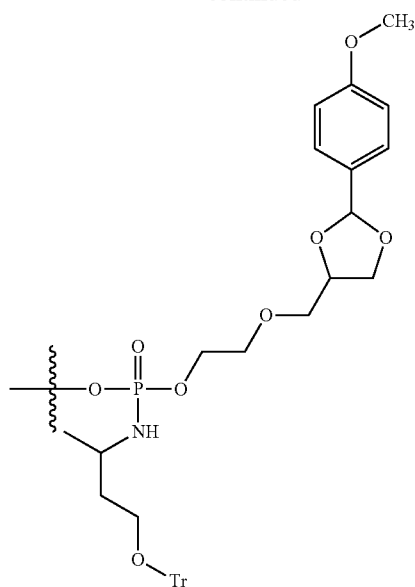
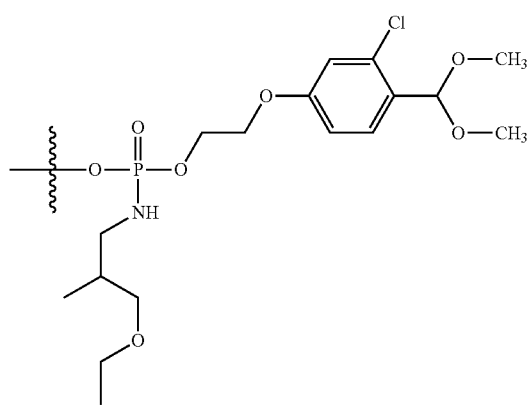
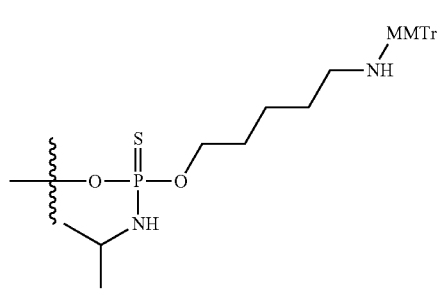
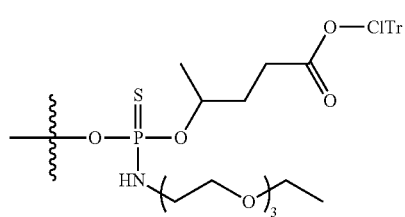
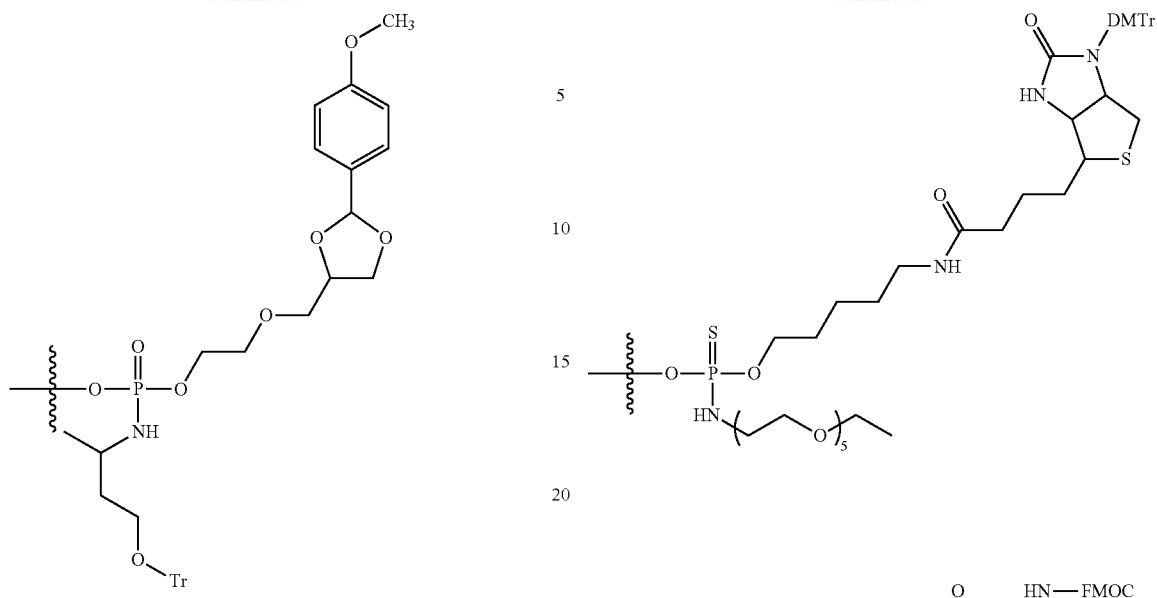
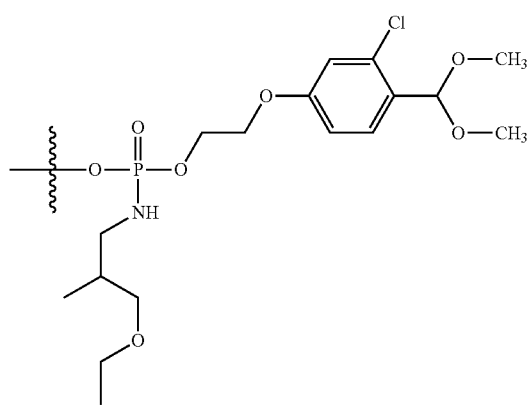
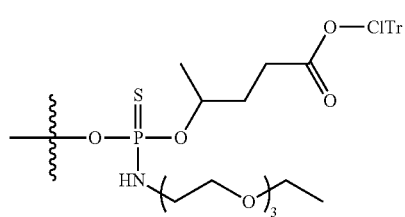

-continued

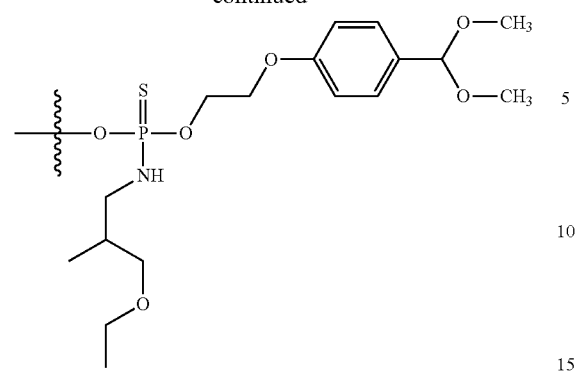
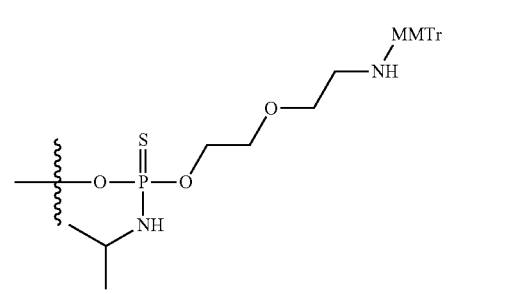
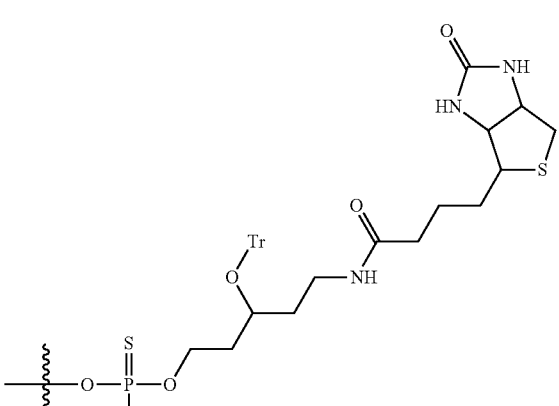
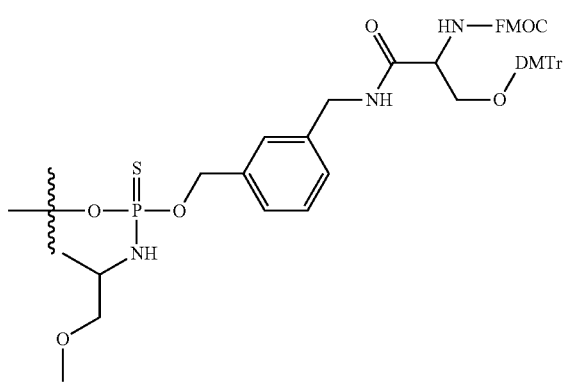

-continued

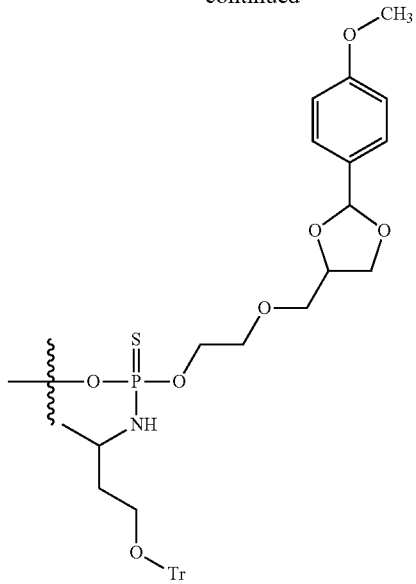
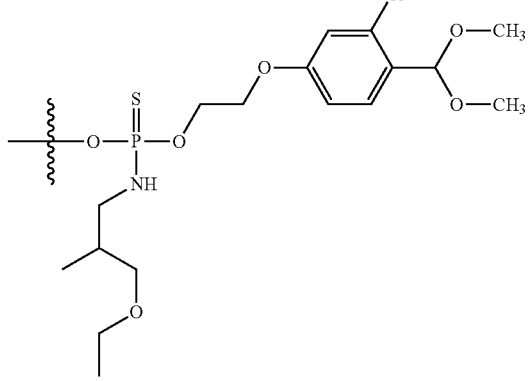

Provided herein is a new type of functional, water-soluble polymer, not belonging to the classes of polypeptides or nucleotides and containing the structure of formula (1):

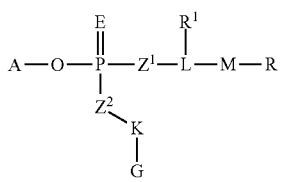

In this schematic picture of such a modified polymer, A is the point of bonding to the terminus of the polymer backbone, E is an oxygen or sulfur atom, K is selected from the group consisting of alkylene, alkyleneoxyalkylene, or an oligomeric form of alkyleneoxyalkylene, G is hydrogen or is selected from the group consisting of an alkoxy and a hydrophobic separation handle, $Z^1$ and $Z^2$ can be oxygen or nitrogen, in such way that both $Z^1$ and $Z^2$ may be oxygen, but when $Z^1$ is NH then $Z^2$ is oxygen, and when $Z^2$ is NH then $Z^1$ is oxygen, L is selected from the group consisting of a divalent radical of a nucleoside, linear alkylene, branched alkylene, alkyleneoxyalkylene, oligomeric form of alkyleneoxyalkylene, arylene, and substituted arylene, M is a protected group that when deprotected is reactive with a biologically active molecule, a group reactive with a biologically active molecule, or detectable functional group, R is a protecting group, activating group, hydrogen or absent. Thus the L-M-R fragment is linked to a terminus of the polymer via a phosphotriester, thiophosphotriester or amidophosphotriester group.

One characteristic of a compound provided herein is that the functional group M, via the group L, is connected to the chain of the polymer via a phosphotriester group or amido phosphodiester, known also as phosphoramidate group. In addition, a derivatized polymer may exist both in an oxy and a thio form. Non-limiting examples of such groups include:

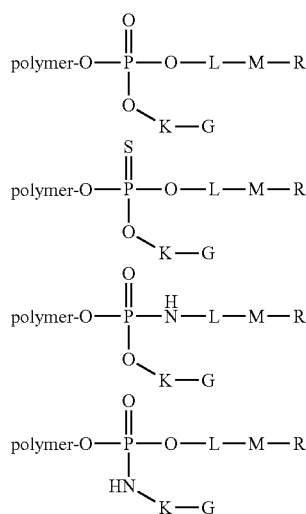

An important class of polymers provided herein, polyethylene glycols (PEG), were previously used in the synthesis of phosphoramidites of the formula: DMTr-O-PEG-O—P(OCE)N(iPr)$_2$. These compounds were used for direct coupling of PEG molecules to synthetic nucleic acids or to a surface of a solid phase. In all reactions, the reactive phosphoramidite group was present at the terminal of the polymer. A polymer substituted with a phosphoramidite group is, however, not a subject of the present disclosure, as the phosphorous atom in the phosphoramidite group is the part of the reactive functionality and not a part of the linker as in the compounds provided herein.

This formal distinction can have a deeper chemical importance. A phosphoramidite group can be designed to work in a completely water-free environment. Upon activation with certain protonating agents/activators a phosphoramidite group can become extremely reactive, and in the presence of water, this reactive function can decompose instantaneously, making this function inappropriate for conjugation to biological material in aqueous solution. Additionally, published PEG phosphoramidites can contain a specially designed, labile protecting group adjacent to the phosphorous atom to convert the intermediate phosphotriester to a phosphodiester. The present document is based, at least in part, on the observation that phosphodiesters are unstable in aqueous biological media such as blood, plasma or cellular extracts, due to the presence of phosphatases and phosphodiesterases. This can preclude phosphodiester linkages as a linking group within a structure of a conjugate, as long as it is aimed for use in biological media. This document, contrary to the existing literature, and contrary to all normal procedures, recommends keeping the phosphate in the form of a phosphotriester or in the form of its amide in order to gain stability of the linking group/conjugate.

Phosphotriester bonds are very rare in nature, existing in most of the cases as cyclic products of RNA transformations. As non-charged variants of nucleotides they gained some attention from those who hoped that it could be possible to use this form of nucleotides as predrugs, which would be transformed in vivo to the active phosphodiester forms. However, acyclic phosphotriesters, lacking specially designed internal features facilitating deprotection, were found completely stable, both chemically at the physiological pH range, and enzymatically in the presence of the most active phosphate hydrolytic enzymes: McGuigan et al., *Nucl. Acids Res.* 1989, 17 (15), 6065-6075; Hecker and Erion, *J. Med. Chem.* 2008, 51, 2328-2345; Conrad et al. *Chem. Bio. Interactions* 1986, 60, 57-65; and Fidanza et al., *Methods in Molecular Biology* 1994, 26, 121-143.

The proposed way of linking a functional group to the polymeric molecule can include combining chemistry typical for nucleic acids with chemistry of polymers and their conjugates. Moreover, this combination can be performed in a way to yield a product with distinctly better characteristics than if this combination of chemistries would proceed following the standard path.

This document also provides methods and materials for introducing of a useful separation handle on the derivatized polymer. This separation handle can be introduced simultaneously with the functional group, so the presence of the separation handle becomes an indicator of successful introduction of the reactive group. If chromatographic properties of a particular separation handle are properly chosen, it is possible to discriminate between non-derivatized, mono-derivatized and multiderivatized (e.g., bis-derivatized) polymers. Most of the separation handles used herein introduce hydrophobic properties to the polymer, as the preferred method for separation of the modified polymers is based on reverse-phase analytical and preparative chromatography. The choice of a proper separation handle comes from consideration of several practical aspects such as:

a) The hydrophobic separation handle can be removed from the polymer after purification in order to liberate the group reactive with a biologically active molecule and to avoid uncontrolled hydrophobic interactions within the conjugate—or more generally to avoid uncontrolled hydrophobic interactions during the interaction of the conjugate with the biological environment. This can preclude work with analogues of mPEG which contain a long hydrophobic alkyl ether chain instead of a methoxy group at one of the polymer termini. For the same reason, protection of an amino group as long chain fatty acid amides is not practical, as this group can be removed only under very extreme conditions.

b) As most of polymers and functional groups lack chromophoric properties, the chromatographic separation of polymers can be difficult. It is, therefore, advantageous if the separation handle introduces additionally some chromophore properties to the polymer. This can make protection of a terminal hydroxyl or thiol group by means of a long chain aliphatic fatty acid ester less interesting.

c) Chemical stability of the hydrophobic separation handle can be easy to control depending on an actual situation. This aspect is related mostly to the stability of other functional groups present in the derivatized polymer.

d) Chromatographic properties of the hydrophobic separation handle, and hence the properties of the derivatized polymer, can be easy to control by chemical modification of the hydrophobic separation handle.

e) Since even relatively stable phosphotriester bonds are slightly labile under high pH conditions, it can be preferred to avoid hydrophobic separation handles that can only be removed under such conditions.

Examples of hydrophobic separation handles that fulfill all these criteria belong to the group of acid labile protecting groups and are known as trityls, substituted trityls (e.g., monomethoxytrityl (MMTr), dimethoxytrityl (DMTr), trimethoxytrityl (TMTr), and p-bromophenacyloxytrityl (BPTr), pixyls and substituted pixyls (see, for example, U.S. Publication No. 2007/0276139). They are all acid labile, with distinct UV chromophore properties. Their acid stability can be easily controlled by the presence of different electron donating or electron withdrawing groups. Introduction of alkoxy chains of different length to the trityl structure is a convenient method for modification of their hydrophobic properties. Most of the Examples presented herein utilize, therefore, trityl groups both for protection of reactive functions and for introduction of an efficient separation handle. This should not be seen as a limitation of this disclosure, as other groups, even those which do not fulfill all the above criteria, may be useful in the present methodology as hydrophobic separation handles. Thus, a general description of a potential hydrophobic separation handle provided herein is: a hydrophobic group that withstands the presence of trivalent phosphorus present in a phosphoramidite or in an activated H-phosphonate, and which can also be employed for chromatographic resolution of modified polymer from the unmodified starting material.

With a few exceptions, there are few limits on the type and character of a functional group M. These exceptions appear in cases when the functional group is very sensitive to reducing conditions and becomes destroyed by the trivalent phosphoramidite group, with concomitant oxidation of phosphorus to the pentavalent oxidation state. The azido group is an example of such a reactive function that cannot be converted to the appropriate phosphoramidite. In fact, trivalent phosphorus of triphenylphosphine is used as an efficient reagent for conversion of an azido group to an amine. The activated dithio group, for example, as in a dithiopyridyl group, is another example that belongs to this category, although simple dithiols could be successfully converted to and delivered in the form of a phosphoramidites. Nevertheless, this disclosure presents also a variant of the above phosphoramidite method that omits the mentioned stability problem, and provides the ability to prepare polymers containing even an azido or activated dithio group.

This method is known as H-phosphonate methodology followed by oxidation of $P^{+3}$ by carbon tetrachloride/amine, and is similar to the phosphoramidite method in the sense that the incoming reagent contains reactive $P^{+3}$ phosphorus, and the phosphorus atom is oxidized during the reaction process to its pentavalent stage. The H-phosphonate methodology will be described in more detail later on in this text.

Many groups reactive with a biologically active molecule of interest need to be protected in order to exist within the structure of phosphoramidite reagent. Examples include, without limitation, amino, aminoxy, hydrazo, hydroxyl, thio, certain fluorophores and carboxy groups. Some of these groups, like biotin, do not demand protection, but can be used in a protected form to obtain some additional effects. In some cases, trityl, substituted trityl, pixyl, and substituted pixyl can be used as protecting groups. One reason for this choice of a protecting group is the possibility for simultaneous introduction of a protecting group that also can be used as a hydrophobic separation handle in a reverse phase (RP) based chromatographic separation process. If separation is not demanded, like in the case where the polymer has only one reactive terminus (e.g., when using mPEG as a polymer backbone), and incorporation of a phosphoramidite may be forced to completion, any protecting group can be used for protection of the group reactive with a biologically active molecule. In particular, trifluoroacetamido and FMOC groups may be used for the protection of amino, aminoxy and hydrazo groups in such phosphoramidites.

The use of phosphoramidites containing a protected group, that when unprotected is reactive with a biologically active molecule, having a hydrophobic protecting group for derivatization of polymers has a clear advantage over other methods. For example, the starting polymer does not have to be partially protected in order to obtain pure, monofunctionalized polymers. The methods work with fully unblocked polymers and improved yield is obtained using an excess of such a non-expensive polymer (e.g., non-derivatized PEG) over the amidite. One value of this method is in the fact that the formed mixture consisting of mono-, bis-, or multi-derivatized polymers can be efficiently separated from each other.

Certain functional groups do not offer a straightforward possibility for introduction of a desired hydrophobic protecting group. To this group belong NHS-esters, most of the fluorophores, iodoacetamido and maleimido groups. Amidites containing these functional groups are not optimal for derivatization of diol-polymers, since the separation of the reaction mixtures can be impossible.

In some cases, polymer diols can be easily converted to certain monoprotected derivatives, and this protection can offer the possibility for using chromatography to obtain pure, temporarily blocked monoderivatized polymers. Even here the separation can be based on hydrophobic interactions between a hydrophobic support and a polymer derivatized with a hydrophobic protecting group acting as a hydrophobic separation handle. Examples of handles used for this purpose include, without limitation, substituted or unsubstituted tritylated hydroxyls, tritylated thiols, and tritylated amines. Introduction of a trityloxy or pixyloxy group onto the terminus of a polymer is straightforward as these polymers usually contain free hydroxyl groups. Introduction of a tritylthio group requires activation of the hydroxyl group by its conversion to a mesylate, tosylate, or by substitution with a halogen. In some cases, this last alternative can be used, as its implementation in the form of a Velsmeier reaction can be economically attractive. The activated polymer can then react with tritylmercaptan as described by Conolly and Rider in *Nucleic Acids Res.* 1985, 13, (12), 4485-4502. A polymer substituted with a thiol group also can be obtained by any of the other described methodologies, and then the thio group can be selectively tritylated in an acidic environment, utilizing the much higher affinity of the thio group over hydroxyl to carbocations. There are two ways to obtain polymers protected on one site with a tritylated amine group. A process is described for direct alkylation of tritylamine with alkyl halides so this method could be used directly in analogy to the above alkylation of tritylmercaptan. On the other hand any appropriate method for partial amination like alkylation of the phthalimide, alkylation of the trifluoracetamide or a Mitsunobu procedure can be applied for preparation of a monoamino polymer. This starting material, even in unpurified form, can be used for obtaining the tritylated amino polymer in a two-step process, starting with sylation of all free hydroxyls in a pyridine solution. All mentioned tritylated or pixylated polymers can be preoperatively purified by RP chromatography to isolate the pure monosubstituted polymer. The described earlier mono-protected polymer derivatives, made by reacting a polymer with a selected phosphoramidite, offer an interesting alternative as a mono-protected polymeric starting material for additional derivatization. Such a polymer can react next with a phosphoramidite to incorporate another functional group, so the final product can contain, for example, two separate phosphotriester linkages.

Monomethoxy PEG (mPEG), or generally monoalkylated polymers, can be used for the same purpose. Methoxy PEG's are used to guarantee monofunctionalization of a polymer. The problem is that such polymers can be contaminated by an unknown and variable amount of bis hydroxyl (diol) polymer. In the case of PEG the existence of the diol form is a consequence of moisture present during the polymerization of the ethyleneoxide, and this can be hard to avoid on an industrial scale. Even the slightest amount of water can result in formation of a hydroxyl anion—an undesired starting point of polymerization. Thus mPEG is not an optimal polymer for preparation of pure monofunctionalized polymers.

Once a polymer is properly monoprotected, however, its conversion to a reactive monofunctional derivative is straightforward. Phosphoramidite chemistry allows incorporation of a reactive functionality with yield and speed that is beyond the competition of other chemical processes, including all sorts of hydroxyl alkylation reactions. Using the proper excess of these reagents, the reported yields exceed 98% for every step in a multistep process and are often nearly quantitative. In cases where only a single incorporation of a phosphoramidite takes place, this reaction can be expected to be quantitative.

There exists also an interesting alternative process to the described above functionalization following the previously described monoprotection. Groups reactive with a biologically active molecule that lack the possibility of carrying a hydrophobic separation handle can be incorporated into a trisubstituted unit having the reactive group of choice, the hydrophobic separation handle and the phosphoramidite group. There are several such units or molecules that can be used as carriers (scaffolds) for the construction of such trisubstituted block reagents. One of the simplest molecules, due to the ease of the chemical manipulations, is the uridine-based scaffold described by Hovinen and Hakala in *Organic Lett.* 2001, 3(16) 2473-2476, where R denotes a reactive group and L is an aliphatic linker to the uridine ring.

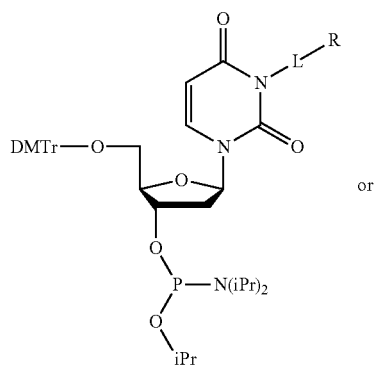

or

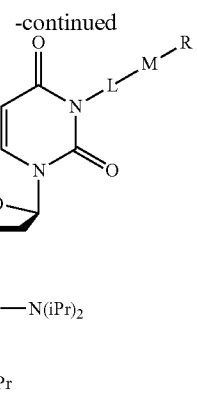

For instance, using reagents belonging to this category, it is possible to prepare, in a single reaction step, polymers covalently bonded to different fluorescent functionalities that can be isolated as a monosubstituted polymeric product.

The chemistry of phosphoramidites is mostly associated with the chemistry of nucleic acids. The very high demands of this multistep process require rather large excess of incoming amidites, and efficient catalysts. Examples of activators includes, without limitation, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), and 4,5-dicyanoimidazole (DCI). Those are often expensive, and if applied to the synthesis of polymers, as in this disclosure, they would noticeably increase the price of the final reagent. However, as the chemistry in the present disclosure can have a single coupling step, and the quantitative yield of the reaction is not always necessary, it is possible to use other less expensive catalysts. The use of pyridinium hydrochloride or even buffered carboxylic acids for activation of phosphoramidites is described and proved, offering high reaction rate, albeit with minimally lower coupling yield.

The choice of an oxidizing reagent is another factor for consideration. Iodine is the simplest alternative, as this reagent can be prepared by dissolving iodine in a mixture of pyridine, tetrahydrofuran and water. Elemental sulfur can be used for phosphite oxidation combined with formation of sulfurized product, but it can be poorly soluble in organic solvents which can be used in the procedures described herein. Other, better soluble and more reactive reagents, like 3H-1,2-benzothiazol-3-one 1,1-dioxide (Beaucage reagent), phenylacetyl disulfide (PADS) or dimethylthiuram (DTD) were developed for this purpose. Thiophosphotriester linkages do not offer very much advantage over the normal phosphotriester linkages, as the latter can already be sufficiently stable, but may offer additional possibilities, e.g. the ability of chemical cleavage of this linkage. Peroxides exemplified by t-butyl hydrogen peroxide or m-chlorobenzoyl peroxide can be used as alternatives for $P^{+3}$ to $P^{+5}$ oxidations. They are colorless, can work under water-free conditions and are often applicable in situations where iodine promoted oxidations may lead to some unwanted side reactions.

It was mentioned earlier that groups reactive with a biologically active molecule which do not tolerate a coexistence with the phosphoramidite group can be attached to the polymer by H-phosphonate chemistry. This method takes advantage of the fact that $P^{+3}$ of the H-phosphonate is actually tetracoordinated, and as such this group can be more stable for oxidation than a phosphate triester or phosphoramidite. The particularly important point is that H-phosphonate does not interact with an azido group like most $P^{+3}$ containing compounds. The use of this methodology for incorporation of the azido group can be, however, combined with the incorporation of a useful hydrophobic separation handle allowing for discrimination between the product and unreacted starting material. Application of a trifunctional reagent, similar to the mentioned uridine derivative, but using a H-phosphonate instead of a phosphoramidite group, could be an alternative. In this case, the activation of the starting H-phosphonate reagent and its reaction with the polymer can be followed by addition of an excess of an appropriate alcohol (e.g., isopropanol) to convert the formed H-phosphonate diester to the desired H-phosphonate triester. The Examples below describe a slightly different procedure. Here, the procedure of introducing an azido group and a hydrophobic separation handle has been divided into two steps, instead of making it in a single step, using a trifunctional reagent. This is not an optimal approach, but it was possible due to very high yield of each reaction. Polymer was first reacted with H-phosphonate of tritylated diethyleneglycol. It is important to use a starting glycol containing more than two carbons; otherwise, the free OH group in the final product, after removal of the trityl group, may destabilize the phosphotriester linkage. Oxidation of $P^{+3}$ to $P^{+5}$ was combined with the introduction of the azido group into the polymer, and it was done according to the described $CCl_4$/pyridine/amine procedure, using 1-amino-6-azidohexane as a source of the azido group. The opposite order of incorporation of reactive groups using H-phosphonate chemistry is also feasible. It is also recognized that H-phosphonate chemistry could be applied for the incorporation of any of existing reactive groups, if other factors of interest like hydrolytic stability of the starting reagents, or costs of syntheses, are deciding.

Conjugates

This document also provides conjugates that include a compound has provided herein and a biologically active molecule. Preparation of such conjugates occurs through a coupling reaction between the group reactive with a biologically active molecule and the biologically active molecule.

Examples of biologically active molecules include therapeutic agents, small molecules such as synthetic drugs, oligo- and polypeptides, oligonucleotides, coding DNA sequences, antisense DNA sequences, mRNAs, antisense RNA sequences, RNAis, and siRNAs, carbohydrates, lipids, growth factors, enzymes, transcription factors, toxins, antigenic peptides (as for vaccines), antibodies, and antibody fragments.

Numerous other examples of biologically active molecules will be apparent to the skilled artisan.

Preparations

Also provided herein are preparations that include a compound or conjugate provided herein. In some embodiments, a preparation can include at least 50% of a compound or conjugate by weight. For example, a preparation can include at least 60%, at least 65%, at least 70%, at least 75% at least 77%, at least 80%, at least 85%, at least 87%, at least 89%, at least 90%, at least 92%, at least 94%, at least 95%, at least 96%, at least 97%, at least 98%, and at least 99% by weight of the compound or conjugate. In some embodiments, the compound or conjugate is essentially pure in the preparation.

A preparation can be a solution, a reaction mixture, a chromatographic eluent, a solid (e.g., a power or crystalline form of the preparation), or any other mixture that includes a compound or conjugate in the appropriate amount or level or purity.

Pharmaceutically Acceptable Salts and Compositions

This document also provides pharmaceutically acceptable salts of the compounds and conjugates provided herein. Examples of pharmaceutically acceptable salts of a compound or a conjugate provided herein include acid addition salts and base salts of the same.

Suitable acid addition salts are formed from acids which form non-toxic salts. Examples include, without limitation, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases which form non-toxic salts. Examples include, without limitation, the aluminium, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulphate and hemicalcium salts.

A conjugate, as provided herein, can be formulated into a pharmaceutical composition that includes an effective amount of a conjugate and a pharmaceutically acceptable excipient. Also provided herein are pharmaceutical compositions that includes an effective amount of a compound as provided herein, wherein M is a detectable functional group, and a pharmaceutically acceptable excipient.

Non-limiting examples of pharmaceutical excipients suitable for administration of the conjugates and compounds provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of a compound or conjugate provided herein. In some embodiments, the excipient is a physiologically acceptable saline solution.

A pharmaceutical composition can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms, Fourth Edition* 1985, 126).

The concentration of a compound or conjugate in a pharmaceutical composition will depend on absorption, inactivation, and excretion rates of the compound or conjugate, the physicochemical characteristics of the compound or conjugate, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or conjugates. The pharmaceutically therapeutically active compounds or conjugates are, in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active compound or conjugate sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing a compound or conjugate as provided herein and optional pharmaceutical adjuvants in a carrier, such as, for example, water, saline, aqueous dextrose, glycerol, glycols, ethanol, and the like, to thereby form a solution or suspension. If desired, a pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing a compound or conjugate provided herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of a compound or conjugate provided herein and methods for their preparation will be readily apparent to those skilled in the art. Such compositions and methods for their preparation may be found, for example, in *Remington's Pharmaceutical Sciences,* 19th Edition (Mack Publishing Company, 1995).

Synthesis

Compounds and conjugates provided herein, including salts thereof, can be prepared using known organic synthesis techniques and can be synthesized according to any of numerous possible synthetic routes. In some embodiments, a compound or conjugate is prepared using a method as provided herein.

The reactions for preparing compounds and conjugates provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry,* $1^{st}$ Ed., Oxford University Press, 2000; *March's Advanced Organic chemistry: Reactions, Mechanisms, and Structure,* $5^{th}$ Ed., Wiley-Interscience Publication, 2001; and Peturssion, S. et al., "*Protecting Groups in Carbohydrate Chemistry,*" *J. Chem. Educ.,* 74(11), 1297 (1997) (each of which is incorporated herein by reference in their entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6) (2004), which is incorporated herein by reference in its entirety) and normal phase silica chromatography.

EXAMPLES

Example 1

Synthesis of isopropyl phosphorodichloridite was performed according to the modified literature procedure of Zwierzak and Koziara, Tetrahedron (1967), 23, 2243-2252.

Dry isopropanol (2 mole) in 100 mL of dry diethyl ether was added dropwise to the vigorously stirred mixture of phosphorus trichloride (4 mole) in 200 mL of diethyl ether at −20° C. The mixture was allowed to warm up to room temperature, and was stirred at this temperature for 4 hours. The mixture was fractionally distilled at normal pressure to obtain the title product by collecting a colorless fraction having bp. 120-125° C.

Example 2

Synthesis of isopropyl, N,N-diisopropylphosphoramidochloridite

Isopropyl phosphorodichloridite (56.5 g, 0.5 mole) in dry diethyl ether (300 mL) was placed in a 1 L round bottom flask and cooled to −30° C. To this vigorously stirred solution, dry diisopropyl amine (109 g, 1 mole) in diethyl ether (200 mL) was added dropwise (2 hr) at the above low temperature. The mixture was then allowed to warm to room temperature and was left at this temperature overnight. The thick white cake of diisopropylammonium hydrochloride was filtered off on a large filter funnel and washed with two portions of ether. The combined ether phase was evaporated and the residue was distilled at lowered pressure collecting a fraction boiling at 83-85° C. (15 Torr).

Example 3

The following is a general procedure used to prepare different phosphoramidite reagents.

An appropriately protected alcohol (1 eq) was placed in a round bottom flask and dried by coevaporation with toluene. The residue was dissolved in dry dichloromethane (DCM) (5 mL/mmole), and dry triethylamine (TEA) (4 eq) was added in one portion. To this solution, stirred at room temperature, isopropyl, N,N-diisopropylphosphoramidochloridite (1.5 eq) in DCM (2 mL/mmole) was added dropwise. The mixture was stirred an additional 30 minutes and when TLC (DCM: Methanol:TEA 95:4:1) showed a complete consumption of the starting alcohol, methanol (5 eq) was added in one portion and the mixture was stirred further for 30 minutes. The reaction mixture was partitioned between dichloromethane and an aqueous solution of sodium bicarbonate. The organic extracts were combined, evaporated, dried by coevaporation with toluene, and purified by flash column chromatography on silica gel using a gradient of ethyl acetate in hexane with addition of 2% TEA as an eluent. The appropriate fractions were collected, and evaporated. The residual solvents were removed under high vacuum, yielding products in the form of thick oils.

The following starting alcohols were prepared according to the published literature and converted to the respective isopropyl phosphoramidites using the procedure outlined above:

1) An amidite useful for introduction of an amino group was prepared by modification of the method of Gaur, *Nucleosides, Nucleotides & Nucleic Acids* (1991), 10, (4), 895-909:

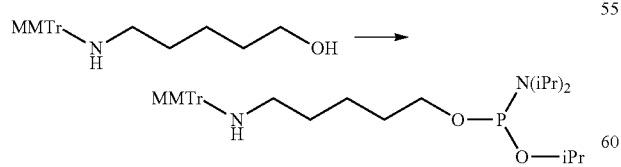

2) An amidite useful for introduction of an aminoxy group was prepared in a process similar to the synthesis of described above for aminating an amidite. The starting aminoxy alcohol was prepared from 6-bromhexanol according to Khomutov, *Zhurnal Obshch Khimyi* 1961, 31, 1992-1995:

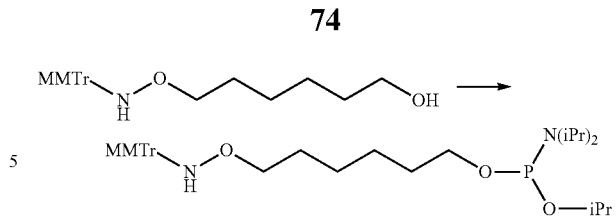

3) An amidite useful for introduction of a hydrazo group was prepared using a modified method of Raddetz et al., *Nucleic Acids Res.* 30, (21), 4793-4802:

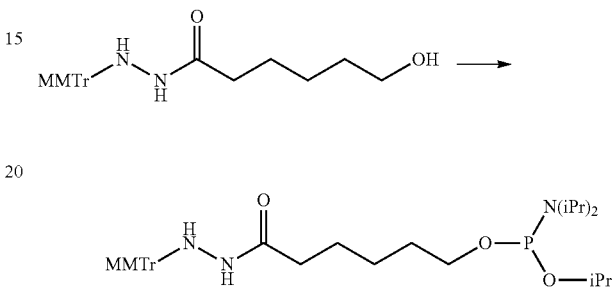

4) An amidite useful for introduction of a thiol was obtained following the procedure described by Connolly and Rider in *Nucleic Acids Res.* 1985, 13, (12), 4485-4502;

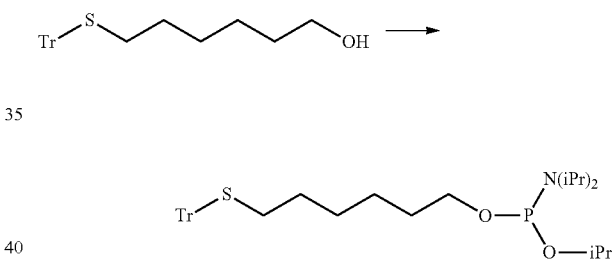

5) An amidite useful for introduction of a carboxyl group was prepared utilizing a chlorotrityl group for protection of a carboxyl group as was described by Kachalova et al. *Helv. Chim. Acta* 2002, 85, 2409-2416:

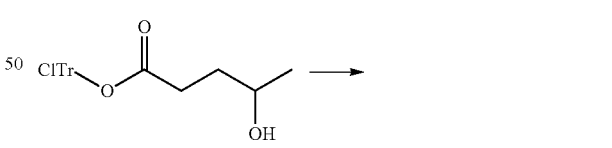

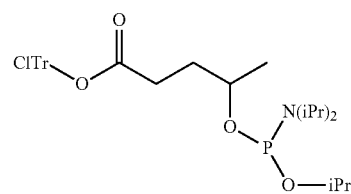

6) An amidite useful for introduction of biotin was prepared following the methodology described by Krempsky et al., *Tet. Lett.*, (1996), 37, (12), 4313-4316:

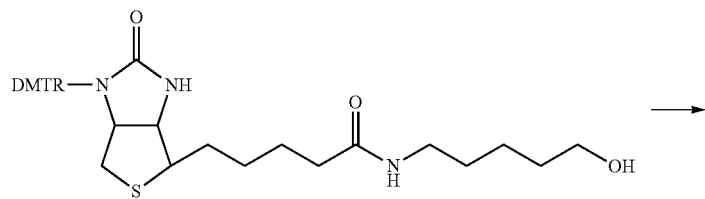

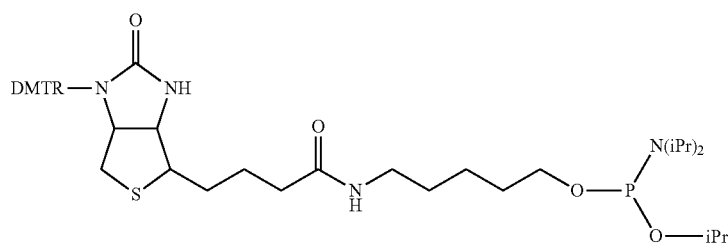

7) The following amidite, prepared in a method analogous to one described by Singh et al. *J. Org. Chem.* 2004, 69, 8544-8546, was used for incorporation of an aliphatic aldehyde group. The aldehyde (as an amide of glyoxalic acid) was obtained after oxidative cleavage of the cis-amine alcohol group:

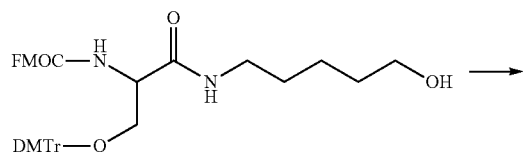

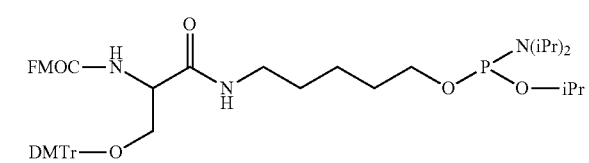

8) The following amidite can be used for incorporation of an aliphatic aldehyde group. This reagent was made in analogy to Spinelli et al. *Nucleosides, Nucleotides and Nucleic Acids* 2007, 26, 883-887. The aldehyde was obtained after acidic hydrolysis of the acetal bond and oxidation of the cis diol system:

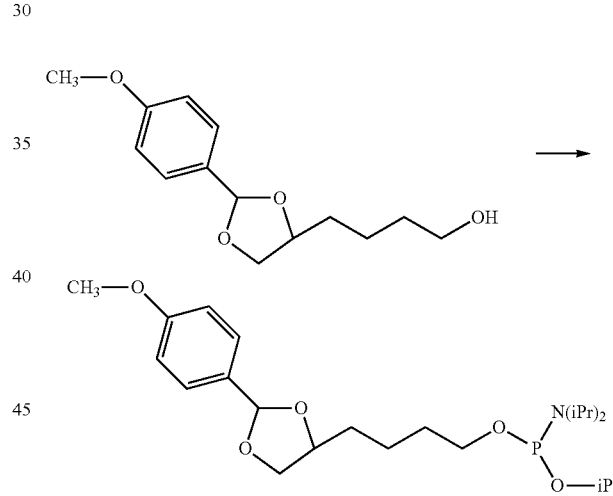

9) The following amidite, prepared by modification of method of Podyminogin et al., *Nucl. Acids Res.* 2001, 29, (24), 5090-5098, can be used for incorporation of an aromatic aldehyde group:

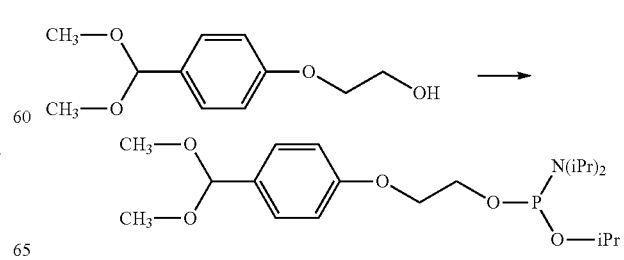

10) An amidite allowing for introduction of an active ester in a single chemical step was prepared analogously to the method described in U.S. Pat. No. 6,320,041:

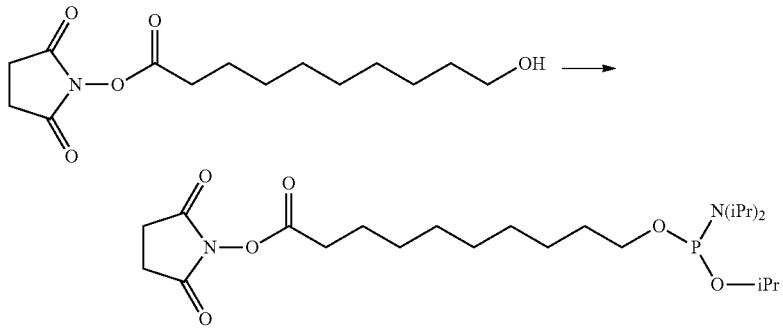

Example 4

The following is a general procedure that was used for the synthesis of pure monosubstituted PEG polymers.

This method utilizes non-derivatized PEG used in excess over the selected phosphoramidite reagent in order to obtain better selectivity. Amidites containing a hydrophobic moiety, like trityl, substituted trityl, long chain fatty esters, or acetals introduce a separation handle that can be used for reversed-phase based chromatographic separation of the product.

Thus PEG 6000 (60 g, 10 mmole, 2 eq.) was dried by double coevaporation with toluene (heating was applied in order to dissolve all material). The residue was dissolved in dry acetonitrile (50 mL) and an appropriate phosphoramidite (5 mmole, 1 eq.) in dry acetonitrile (30 mL) was added in one portion. To this clear solution, stirred at room temperature, a solution of 4,5-dicyanoimidazole (5.9 g, 50 mmol, 10 eq.) in acetonitrile was added in a single portion and the mixture was stirred for 15 minutes. Reaction was stopped by addition of a solution of iodine (0.1 M, 1.2 eq) in THF:pyridine:water (10:10:1) and the brownish solution was stirred for 3 minutes. Aqueous solution of sodium bisulfite was added in small portions until decolorization of the reaction mixture. After evaporation of most of the volatile matter, the residue was dissolved in dichloromethane and extracted with a saturated aqueous solution of sodium bicarbonate. The evaporated organic phase was dried by coevaporation with toluene, and the residue was crystallized from isopropanol. The isolated crystals were dissolved in a small amount of dichloromethane and precipitated by addition of diethyl ether. The final mixture, being a composition containing a free non-derivatized PEG, mono- and bis-derivatized PEG, was preperatively purified by reverse-phase chromatography. Fractions containing the desired product were evaporated, dried and precipitated from diethyl ether. When removal of the acid labile separation handle was required the polymer is dissolved in isopropanol (with slight heating) and a 5% solution of trichloracetic acid in isopropanol was added. The mixture is cooled down in the freezer to obtain a deprotected crystalline product. If a TLC test (silicagel plates in 10% MeOH:DCM) for the purity of the product still showed the presence of the trityl protecting group, the procedure of acidic deprotection was repeated. Deprotection of other functionalities were performed following the literature procedures as far as was possible, but with some modifications:

1) Trityl protected thiol modified polymer was deprotected with a silver nitrate solution in water. After 30 minutes the solution was treated with dithiotreithiol (2 eq. to the amount of silver ions added) and the pH was raised to 9.0 by addition of potassium carbonate. After 30 minutes, the mixture was filtered through a pad of celite and extracted by dichloromethane. The organic phase was evaporated and thiolated PEG was crystallized from isopropanol.

2) Polymers modified with different aldehyde-introducing phosphoramidites were first treated with acid to remove the trityl or the acetal function. In the case of reagent 7 (Example 3) the FMOC group was removed by treatment of the polymer with 10% piperidine in DCM for 4 hours, followed by quick evaporation of the volatile matter and crystallization of the residue from isopropanol. The final conversion of the cis-amino alcohol or cis-diol to the aldehyde was done by means of 10 mM sodium periodate.

Example 5

Pure, mono-substituted PEG molecules used for further derivatization were prepared as follows.

Certain PEG derivatives can be prepared in a large scale and at reasonably low cost. These derivatives can be regarded by themselves as valuable modifications, but also as a good monovalent starting material, well suited for further derivatization. This Example provides for the preparation of three such derivatives 1) Mono DMTr-O-Substituted, Linear PEG.

An appropriate PEG (100 g, 2 eq) was dried by double coevaporation with dry pyridine, dissolved in pyridine (100 mL), and DMTrCl (1 eq) was added to the stirred mixture at room temperature. The yellow solution was stirred for 24 hours and methanol (10 mL) was added. The reaction mixture was stirred for an additional 60 minutes, evaporated, dissolved in dichloromethane, and treated with an aqueous solution of sodium bicarbonate. The organic phase was evaporated, dried by coevaporation with toluene, and all PEG was isolated after precipitation from diethyl ether. The collected mixture of PEG's was purified by reverse-phase chromatography.

2) Mono MMTr-NH-Substituted, Linear PEG.

A commercial monoamino substituted PEG (1 eq) or a material prepared according to any of existing procedures, was dried by double coevaporation with dry pyridine. The residue was dissolved in pyridine (10 mL/mmole of PEG) and trimethylchlorosilane (TMSCl) (4 eq) was added. The mixture was stirred at room temperature for 4 hours and MMTrCl (1.5 eq) was added. The reaction mixture was stirred overnight, and then methanol (50 eq) was added and the mixture was stirred for an additional two hours. The total PEG was isolated after evaporation, drying by coevaporation with toluene, crystallization from isopropanol and precipitation from diethylether. The collected mixture of PEG's was purified by reverse-phase chromatography.

3) Mono Tr-S-Substituted, Linear PEG.

An appropriate, non-derivatized PEG was dried by coevaporation with toluene and dissolved in dry DMF (5 mL/mmole). To this stirred solution at room temperature a preformed solution of phosphoroxychloride (0.4 eq) in dry DMF (5 mL/mmole) was added and stirring was continued for 6 hours. Most of the solvent was then evaporated, and the residue was treated using a saturated aqueous sodium bicarbonate solution. Polyethylene glycol was extracted with dichloromethane and concentrated by evaporation of all volatile matter. The reaction mixture, containing the monochloroderivatized PEG was dissolved in ethanol (10 mL/mmole). Triphenylmethyl mercaptan (1.3 eq. to the starting PEG) was suspended in ethanol (10 mL/mmole) and converted to the sodium salt by addition of an equivalent amount of sodium hydroxide dissolved in a small amount of water. The salt was combined with the ethanolic solution of PEG and the mixture was stirred overnight. After evaporation of ethanol, the residue was partitioned between dichloromethane and aqueous sodium bicarbonate. The organic phase was evaporated and the residue was crystallized from isopropanol, followed by precipitation of total PEG from diethyl ether. The collected mixture of PEG's was purified by reverse-phase chromatography.

Example 6 a) Conversion of monosubstituted PEG to bis-derivatized PEG was performed using the following method.

A one equivalent of commercial methyl PEG (mPEG), (or any of partially protected PEG's from the Examples 4 or 5), was dried by coevaporation with toluene, and the polymer was dissolved in dry acetonitrile (5 mL/mmole). The modifying phosphoramidite (2-3 eq.) in dry acetonitrile (3 mL/mmole) was added, followed by a suitable activator (10-15 eq.) and the reaction mixture was stirred at RT for 15 minutes. At this point all reactions were analyzed by fast reversed-phase analytical chromatography that showed disappearance of all starting material and formation of more hydrophobic product. Reaction was quenched by addition of an oxidizing iodine solution (1.5 eq. to the amount of the phosphoramidite) or t-butylhydrogenperoxide (4 eq to the amount of the phosphoramidite) in cases when the synthesized product did not tolerate iodine or water. The iodine-treated reaction mixtures were evaporated, dissolved in dichloromethane, decolorized with bisulfite, and the organic phase was evaporated. The t-butylhydrogenperoxide treated mixtures were evaporated directly. Both mixtures were partially purified by crystallization from isopropanol, followed by precipitation from diethyl ether to obtain a pure, mono-functionalized, bis-substituted PEG. An azeotropically dried PEG was dissolved in dry acetonitrile (5 mL/mmole). The modifying phosphoramidite (1.0 eq.) in dry acetonitrile (3 mL/mmole) was added, followed by a suitable activator (10-15 eq.) and the reaction mixture was stirred at RT for 30 minutes. Reaction was quenched by addition of an oxidizing iodine solution (1.5 eq. to the amount of the phosphoramidite) or t-butyl hydrogen peroxide (4 eq to the amount of the phosphoramidite) in cases when the synthesized product did not tolerate iodine or water. The iodine-treated reaction mixtures were evaporated, dissolved in dichloromethane, decolorized with bisulfite, and the organic phase was evaporated. The t-butylhydrogenperoxide treated mixtures were evaporated directly. Both mixtures were partially purified by crystallization from isopropanol, followed by precipitation from diethyl ether to obtain reaction mixture free of low molecular components. This mixture was separated on an analytical and on a preparative RP chromatographic system which allow for isolation of pure monosubstituted product. This methodology could be easy applied for amidites introducing amino, hydroxylamino, hydrazo, carboxyl, aldehyde and the biotin group. The isolated products could be deprotected upon treatment with appropriate acidic conditions, followed by precipitation of the deprotected PEG from diethylether, or the non-deprotected material could be used in preparation of hetero-bis-functionalized polymer as presented bellow.

c) Using the above idea of conversion of PEG diol into a pure, mono-functionalized product from Example 6b) with subsequent derivatization with another reagent, the following compounds were prepared.

1) MMTr—NH—$(CH_2)_5$—O—PO—(O-iPr)O-PEG-O(O-iPr)-PO—O—$(CH_2)_6$—O—NH-MMTr
2) MMTr—NH—$(CH_2)_5$—O—PO—(O-iPr)O-PEG-O(O-iPr)-PO—O—$CH(CH_3)(CH_2)_2$—COO—ClTr.

The second derivatization were performed as in Example 6a) using excess of the second reagent over PEG to insure quantitative conversion to the double functionalized product The final compound was analyzed by HPLC, but any preparative chromatography at this stage was not needed.

Example 7

The following describes methods used to introduction functional groups which were not stable in the presence of the phosphoramidite group.

Diethylene glycol protected on one end with a DMTr group, and containing a H-phosphonate group at the other end, was synthesized from a tritylated diol by a standard $PCl_3$/triazole method according to Garegg et al., *Chem. Scr.* 1986, 26, 59-62.

The above H-phosphonate (3 eq) and mPEG (1 eq) were dried by repeated coevaporation with dry pyridine. The residue was dissolved in pyridine (10 mL/mmole) and treated with pivaloyl chloride (9 eq). The mixture was stirred at room temperature for 2 hours and the reaction was quenched by addition of triethylammonium bicarbonate (TEAB) (1 M, 5 mL/mmole). The reaction mixture was concentrated and partitioned between dichloromethane and diluted TEAB. The organic phase was evaporated, the residue was dried by repeated coevaporation with toluene, and total PEG was purified by precipitation from diethyl ether. The isolated precipitate was filtered, dissolved in pyridine/carbon tetrachloride 2:1 and 1-amino-6-azidohexane (4 eq.) was added. The stirred mixture was left overnight at room temperature. The mixture was evaporated, coevaporated with water, and the residual material was treated with an aqueous ammonia solution (25%, 20 mL/mmole) for 4 hours at room temperature in order to cleave the residual non-oxidized H-phosphonate dimer. Ammonia was evaporated and the resulting crude product was purified by means of preparative reverse-phase chromatography. Final removal of the DMTr group and precipitation of the PEG gave the pure azido modified product.

1) An essentially pure, modified polymer, comprising a water soluble, non peptidic and non nucleotidic, linear or branched polymer backbone, containing from 2 and up to 100 termini, and having at least one terminus being covalently bonded to the structure:

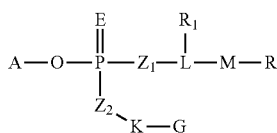

wherein:
- A is the point of bonding to the terminus of the polymer backbone;
- E is oxygen or sulfur;
- K is selected from the group consisting of linear alkyl, branched alkyl, alkyloxyalkyl, or oligomeric form of alkyloxyalkyl;
- G is none, or is selected from the group consisting of an alkoxy, trityloxy or substituted trityloxy group;
- $Z_1$ and $Z_2$ are O or NH in such a way that both $Z_1$ and $Z_2$ may be O, but when $Z_1$ is NH then $Z_2$ is O, and when $Z_2$ is NH then $Z_1$ is O.
- L is selected from the group consisting of linear alkyl, branched alkyl, nucleoside, alkyloxyalkyl, oligomeric form of alkyloxyalkyl, aryl and substituted aryl;
- M is a group reactive with a biologically active molecule or detectable functional group;
- R is selected from a group consisting of protecting groups, hydrophobic separation handles, activating groups, hydrogen or none, $R_1$ is a hydrophobic separation handle or none, and both R and $R_1$ can coexist providing that there is only one hydrophobic separation handle within the molecule or the hydrophobicity of either of these groups is substantially higher than the other;

2) The modified polymer of claim 1, wherein the functional group M is selected from the group consisting of hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide, biotin or a fluorophore.

3) The modified polymer of claim 1, wherein the group K is selected from the group consisting of methyl, ethyl, propyl, isopropyl, butyl, isobutyl, sec-butyl, tert-butyl, hexyl, or a residue from diethylene glycol, triethylene glycol, tetraethylene glycol or hexaethylene glycol.

4) The modified polymer of claim 1, wherein the group L is $C_1$-$C_{12}$ alkyl or substituted alkyl.

5) The modified polymer of claim 1, wherein the group R is selected from trityl, monoalkoxytrityl, dialkoxytrityl, pixyl, alkoxypixyl, FMOC, trifluoroacetyl, acetal, cyclic acetal or combinations thereof 6) The modified polymer of claim 1, wherein, for the functional group M being carboxyl, the group R is selected from the group consisting of chlorotrityl, trityl, N-hydroxysuccinimidyl, p-nitrophenyl, pentachlorophenyl, simple non-activating alkyls selected from the group of $C_1$-$C_{18}$ alkyls or none.

7) The modified polymer of claim 1, wherein the non peptidic and non nucleotidic polymer backbone is selected from the group consisting of poly(alkylene glycol), poly(oxyethylated polyol), poly(olefinic alcohol), poly(α-hydroxy acid), poly(vinyl alcohol), polyoxazoline, and copolymers and mixtures thereof 8) The modified polymer of claim 1, wherein the non peptidic and non nucleotidic polymer backbone is poly(ethylene glycol).

9) The modified polymer of claim 8, wherein the poly(ethylene glycol) has an average molecular weight from about 500 Da to about 100000 Da.

10) An essentially pure, linear form of modified polymer of claim 1, wherein the two termini of the polymer are modified non-symmetrically with two different functional groups and wherein the two functional groups are linked to the polymer as in the structure:

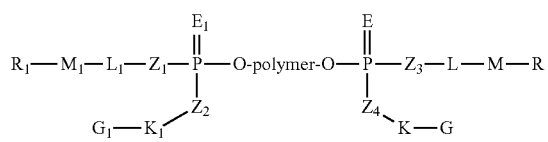

wherein:
- M and $M_1$ are two different functional groups reactive with a biologically active molecule or detectable functional groups;
- E and $E_1$ are independently oxygen or sulfur;
- The pair $Z_1$ and $Z_2$ are independent from the pair $Z_3$ and $Z_4$ and both $Z_1$ and $Z_2$ may be O, but when $Z_1$ is NH then $Z_2$ is O, and when $Z_2$ is NH then $Z_1$ is O, similarly for a pair of $Z_3$ and $Z_4$—both $Z_3$ and $Z_4$ may be O, but when $Z_3$ is NH then $Z_4$ is O, and when $Z_4$ is NH then $Z_3$ is O;
- L and $L_1$ are independently selected from the group consisting of linear alkyl, branched alkyl, alkyloxyalkyl, oligomeric form of alkyloxyalkyl, aryl and substituted aryl;
- R and $R_1$ are independently protecting groups, activating groups or none;
- K and $K_1$ are independently selected from the group consisting of linear alkyl, branched alkyl, alkyloxyalkyl, or oligomeric form of alkyloxyalkyl;
- G and $G_1$ are independently selected from the group consisting of none, an alkoxy, trityloxy or substituted trityloxy group;
- L-M-R and $L_1$-$M_1$-$R_1$ fragments are linked to the respective terminus of the said polymer via phosphotriester, thiophosphotriester or amidophosphotriester bonds;

11) The modified polymer of claim 10, wherein the two different functional groups M and $M_1$ are selected independently from the group consisting of hydroxyl, amine, thiol, carboxyl, aldehyde, glyoxal,dione, alkenyl, alkynyl, alkedienyl, azide, acrylamide, vinyl sulfone, hydrazide, aminoxy, maleimide, dithiopyridine, iodoacetamide, biotin or a fluorophore.

12) The modified polymer of claim 10, wherein the group K is selected from the group consisting of methyl, ethyl, propyl, isopropyl, butyl, isobutyl, sec-butyl, tert-butyl, hexyl, or a residue from diethylene glycol, triethylene glycol, tetraethylene glycol or hexaethylene glycol.

13) The modified polymer of claim 10, wherein the group L is $C_1$-$C_{12}$ alkyl or substituted alkyl.

14) The modified polymer of claim 10, wherein the group R is selected from trityl, monoalkoxytrityl, dialkoxytrityl, pixyl, alkoxypixyl, FMOC, trifluoroacetyl, acetal, cyclic acetal or combinations of thereof.

15) The modified polymer of claim 10, wherein, for the functional group M being carboxyl, the group R is selected from the group consisting of chlorotrityl, trityl, N-hydroxysuccinimidyl, p-nitrophenyl, pentachlorophenyl, simple non-activating alkyls selected from the group of $C_1$-$C_{18}$ alkyls or none.

16) The modified polymer of claim 10, wherein the polymer is poly(ethylene glycol).

17) The modified polymer of claim 16, wherein the poly(ethylene glycol) has an average molecular weight from about 500 Da to about 100000 Da.

18) An essentially pure, linear form of modified polymer of claim 1, wherein the two termini of the polymer are modified non-symmetrically with two different functional groups and wherein the two functional groups are linked to the polymer as in the structure:

$$R_2-M_2\text{-polymer-}O-\overset{\overset{E}{\|}}{\underset{\underset{K-G}{Z_2}}{P}}-Z_1-L-M-R$$

wherein:
M and $M_2$ are two different functional groups reactive with a biologically active molecules or M is a detectable functional group;
E is O or S;
K is selected from the group consisting of linear alkyl, branched alkyl, alkyloxyalkyl, or oligomeric form of alkyloxyalkyl;
G is none or is selected from the group consisting of an alkoxy, trityloxy, monoalkoxy substituted trityloxy group or dialkoxy substituted trityloxy group;
$Z_1$ and $Z_2$ are O or NH in such way that both $Z_1$ and $Z_2$ may be O, but when $Z_1$ is NH then $Z_2$ is O, and when $Z_2$ is NH then $Z_1$ is O;
L is selected from the group consisting of linear alkyl, branched alkyl, alkyloxyalkyl, oligomeric form of alkyloxyalkyl, aryl and substituted aryl;
R is a protecting group, activating group, hydrogen or none;
L-M-R fragment is linked to the first terminus of the said polymer via phosphotriester, thiophosphtriester or amidophosphotriester;
$M_2$ is O, S or NH;
$M_2$ is linked directly to the second terminus of the polymer, and not via phosphotriester, thiophosphtriester or amidophosphotriester;
$R_2$ is a protecting group or none.

19) The modified polymer of claim 18, wherein the functional group M is selected from the group consisting of hydroxyl, amine, thiol, carboxyl, aldehyde, glyoxal,dione, alkenyl, alkynyl, alkedienyl, azide, acrylamide, vinyl sulfone, hydrazide, aminoxy, maleimide, dithiopyridine, iodoacetamide or biotin.

20) The modified polymer of claim 18, wherein the group $R_2$ is selected from the group consisting of trityl, monoalkoxytrityl, dialkoxytrityl, pixyl, alkoxypixyl, FMOC, alkylcarboxyl, benzoyl, tetrahydropyranyl, methyl or none.

21) The modified polymer of claim 18, wherein the polymer is poly(ethylene glycol).

22) The conjugate of any polymer of claims 1 to 18 with a biologically active molecule wherein said biologically active molecule is selected from the group consisting of enzymes, peptides, polypeptides, nucleotides, oligonucleotides, polynucleotides and low molecular weight drugs.

23) A method of synthesizing a substantially pure, water soluble polymer of claim 1, said method comprising the steps of:
a) contacting the water soluble polymer, of non-peptidic and non-nucleotidic type, and having linear or branched polymer backbone, and containing from 2 and up to 100 termini, in a water free solvent, with a selected modifying reagent in form of the phosphoramidite derivative as in the structure:

$$\underset{R_4}{\overset{R_3}{\diagdown}}N-P-\underset{\underset{K-G}{O}}{O}-L-M-R$$

wherein:
$R_3$ and $R_4$ are isopropyls or are a part of morpholine ring.
b) starting reaction by addition of an activating reagent.
c) oxidation of $P^{+3}$ to $P^{+5}$ by addition of an oxidizing reagent.
d) optional chromatographic purification of the protected polymer.
e) removal of the protecting groups.

24) Method of claim 23 wherein the activating reagent is selected from tetrazole, 2-ethylthiotetrazole, 2-bezylthiotetrazole, 4,5-dicyanoimidazole, "Activator 42", pyridinium hydrochloride or pyridinium trifluoroacetate 25) Method of claim 23 wherein the oxidizing reagent is selected from a group consisting of iodine, water peroxide, t-butyl hydrogen peroxide, acetone peroxide, sulfur and thiuram disulfide.

26) Method of claim 23, wherein the ratio between the polymer and the phosphoramidite is from 1:1 to 10:1 in order to facilitate formation of monosubstituted product.

27) A method of synthesizing a substantially pure, water soluble polymer of claim 10, said method comprising the steps of:
a) reacting the water soluble polymer, of non-peptidic and non-nucleotidic type, having linear polymer backbone, and containing two reactive termini, in a water free solvent, with a selected first modifying reagent in form of the phosphoramidite derivative, under conditions that facilitate formation of mono-derivatized product.
b) chromatographic isolation of the monoderivatized polymer.
c) reacting the monoderivatized product with a second modifying reagent in the form of phosphoramidite derivative, under conditions that facilitate the quantitative conversion to the double modified polymer.
d) isolation of the double modified polymer by precipitation or crystallization.

28) A method of synthesizing a substantially pure, water soluble polymer of claim 18, said method comprising the steps of:
a) reacting the substantially pure, linear polymer, substituted at the first terminus with a function R-$M_2$, with a selected modifying reagent in form of the phosphoramidite derivative under conditions facilitating the quantitative conversion of the mono substituted polymer to the double modified polymer.
b) isolation of the double modified polymer by precipitation or crystallization.

29) The use of any material of claim 1 to claim 28 for formation of a conjugate between this material and a biologically active molecule, wherein said biologically active molecule is selected from the group consisting of enzymes, peptides, polypeptides, nucleotides, oligonucleotides, polynucleotides and low molecular weight drugs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising a water-soluble, non-peptidic, and non-nucleotidic polymer backbone having at least one terminus covalently bonded to a structure of formula (1):

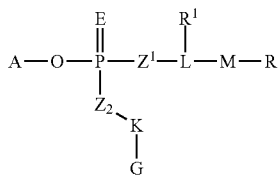

or a salt thereof,
wherein:
A is the point of covalent bonding to the terminus of the polymer backbone;
E is O;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently O;
L is a divalent radical of an alkylene;
M is a protected carboxyl moiety;
R is selected from the group consisting of: a protecting group and a hydrophobic separation handle;
$R^1$ is absent or a hydrophobic separation handle; and
wherein no more than one of R, $R^1$, and G is a hydrophobic separation handle.

2. The compound of claim 1, wherein the polymer has from 2 to 100 termini.

3. The compound of claim 1, wherein only one termini of the polymer backbone is covalently bonded to the structure of formula (1).

4. The compound of claim 1, wherein the polymer backbone has two termini.

5. The compound of claim 4, wherein only one termini of the polymer backbone is covalently bonded to the structure of formula (1).

6. The compound of claim 4, wherein both termini of the polymer backbone are covalently bonded to the structure of formula (1).

7. The compound of claim 1, wherein K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

8. The compound of claim 1, wherein G is a substituted or unsubstituted trityloxy.

9. The compound of claim 1, wherein L is a substituted or unsubstituted $C_1$-$C_{12}$ alkylene.

10. The compound claim 1, wherein R is selected from the group consisting of: trityl, monoalkoxytrityl, dialkoxytrityl, pixyl, alkoxypixyl, fluorenylmethyloxycarbonyl, trifluoroacetyl, acetal, and cyclic acetal.

11. The compound of claim 1, wherein R is selected from the group consisting of: chlorotrityl, trityl, N-hydroxysuccinimidyl, p-nitrophenyl, pentachlorophenyl, and an unsubstituted $C_1$-$C_{18}$ alkyl.

12. The compound of claim 1, wherein said polymer backbone is selected from the group consisting of poly(alkylene glycol), poly(oxyethylated polyol), poly(olefinic alcohol), poly(α-hydroxy acid), poly(vinyl alcohol), polyoxazoline, and copolymers.

13. The compound of claim 1, wherein said polymer backbone is poly(ethylene glycol).

14. The compound of claim 13, wherein said poly(ethylene glycol) has an average molecular weight from about 500 Da to about 100,000 Da.

15. A preparation comprising a compound comprising a water-soluble, non-peptidic, and non-nucleotidic polymer backbone having at least one termini covalently bonded to a structure of formula (1):

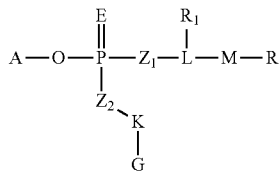

or a salt thereof,
wherein:
A is the point of bonding to the terminus of the polymer backbone;
E is O;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently O;
L is a divalent radical of an alkylene;
M is a protected carboxyl moiety;
R is selected from the group consisting of: a protecting group and a hydrophobic separation handle;
$R^1$ is absent or a hydrophobic separation handle;
provided that only one of R and $R^1$ is a hydrophobic separation handle or the hydrophobicity of one of R or $R^1$ is higher than the other;
wherein said preparation comprises at least 50% by weight of said compound; and
wherein no more than one of R, $R^1$, and G is a hydrophobic separation handle.

16. The preparation of claim 15, wherein the compound is essentially pure.

17. A compound of formula (2):

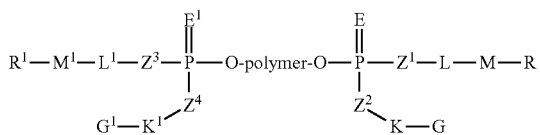

or a salt form thereof,
wherein:
polymer is a linear, water-soluble, non-peptidic, and non-nucleotidic polymer backbone, wherein each linking group is bonded at a different terminus of said polymer;
E is O; and
$E^1$ is O or S;
K and $K_1$ are independently selected from the group consisting of: alkylene, alkyleneoxyalkylene, and oligomeric alkyleneoxyalkylene;
G and $G_1$ are independently absent or are selected from the group consisting of: alkoxy and a hydrophobic separation handle;
$Z^1$ and $Z^2$ independently are O;
$Z^3$ and $Z^4$ are independently selected from O and NH, wherein no more than one of $Z^3$ and $Z^4$ is NH;
L is a divalent radical of a alkylene;
$L^1$ is selected from the group consisting of: a divalent radical of a nucleoside, alkylene, alkyleneoxyalkylene, oligomeric alkyleneoxyalkylene, and unsubstituted and substituted arylene;
M is a protected carboxyl moiety;
$M^1$ is selected from a protected group that when deprotected is reactive with a biologically active molecule, a group reactive with a biologically active molecule, or a detectable functional group;
wherein M and $M^1$ are different;
R is a protecting group;
$R^1$ is absent, hydrogen, a protecting group, or an activating group;
wherein when $M^1$ is a protected group that when deprotected is reactive with a biologically active molecule, then $R^1$ is a protecting group or a hydrophobic separation handle;
wherein when $M^1$ is a group reactive with a biologically active molecule, $R^1$ is absent, hydrogen, or an activating group; and
wherein when $M^1$ is a detectable functional group, $R^1$ is absent or hydrogen.

18. A preparation comprising a compound of formula (2):

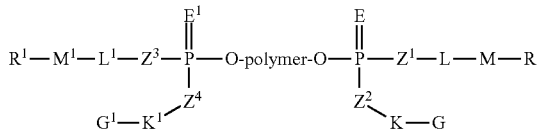

or a salt form thereof,
wherein:
polymer is a linear, water-soluble, non-peptidic, and non-nucleotidic polymer backbone, wherein each phosphonate-derived functional group is bonded at a different terminus of said polymer;
E is O; and
$E^1$ is O or S;
K and $K_1$ are independently selected from the group consisting of: alkylene, alkyleneoxyalkylene, and oligomeric alkyleneoxyalkylene;
G and $G_1$ are independently absent or are selected from the group consisting of: alkoxy and a hydrophobic separation handle;
$Z^1$ and $Z^2$ independently are O;
$Z^3$ and $Z^4$ are independently selected from O and NH, wherein no more than one of $Z^3$ and $Z^4$ is NH;
L is a divalent radical of a alkylene;
$L^1$ is selected from the group consisting of: a divalent radical of a nucleoside, alkylene, alkyleneoxyalkylene, oligomeric alkyleneoxyalkylene, and unsubstituted and substituted arylene;
M is a protected carboxyl moiety;
$M^1$ is selected from a protected group that when deprotected is reactive with a biologically active molecule, a group reactive with a biologically active molecule, or a detectable functional group;
wherein M and $M^1$ are different;
R is a protecting group;
$R^1$ is absent, hydrogen, a protecting group, or an activating group;
wherein when $M^1$ is a protected group that when deprotected is reactive with a biologically active molecule, then $R^1$ is a protecting group or a hydrophobic separation handle;
wherein when $M^1$ is a group reactive with a biologically active molecule, $R^1$ is absent, hydrogen, or an activating group; and
wherein when $M^1$ is a detectable functional group, $R^1$ is absent or hydrogen; and
wherein said preparation comprises at least 50% by weight of said compound.

19. A compound of formula (3):

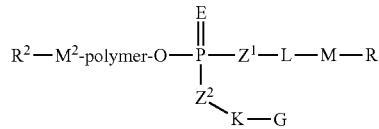

or a salt form thereof,
wherein:
polymer is a linear, water-soluble, non-peptidic, and non-nucleotidic polymer backbone, wherein $M^2$ and the phosphonate-derived functional group are bonded at a different terminus of said polymer;
E is O;
$E^1$ is O or S;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently O;
L is a divalent radical of an alkylene;
M is a protected carboxyl moiety;
$M^2$ is selected from O, S or NH; and
R is a protecting group or a hydrophobic separation handle;
$R^2$ is hydrogen or a protecting group.

20. A preparation comprising a compound of formula (3):

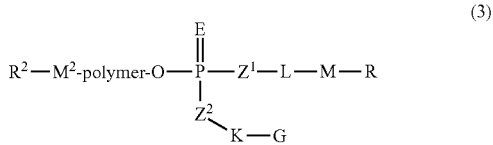

or a salt form thereof,
wherein:
polymer is a linear, water-soluble, non-peptidic, and non-nucleotidic polymer backbone, wherein $M^2$ and the phosphonate-derived functional group are bonded at a different terminus of said polymer;
E is O and $E^1$ is O or S;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are independently O;
L is a divalent radical of an alkylene;
M is a protected carboxyl moiety;
$M^2$ is selected from O, S or NH; and
R is a protecting group or a hydrophobic separation handle;
$R^2$ is hydrogen or a protecting group;
and
wherein said preparation comprises at least 50% of said compound.

21. The compound of claim 1, wherein the hydrophobicity of one of R or $R^1$ is higher than the other.

22. The compound of claim 17, wherein one of $Z^3$ and $Z^4$ is NH and the other is O.

23. The compound of claim 17, wherein $Z^3$ is O and $Z^4$ is O.

24. The compound of claim 17, wherein said group reactive with a biologically active molecule is selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

25. The compound of claim 17, wherein K or $K^1$ is independently selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

26. The compound of claim 17, wherein G or $G^1$ is independently a substituted or unsubstituted trityloxy.

27. The compound of claim 17, wherein $L^1$ is a substituted or unsubstituted $C_1$-$C_{12}$ alkylene.

28. The compound of claim 17, wherein R or $R^1$ is independently selected from the group consisting of: trityl, monoalkoxytrityl, dialkoxytrityl, pixyl, alkoxypixyl, fluorenylmethyloxycarbonyl, trifluoroacetyl, acetal, cyclic acetal, and combinations of thereof.

29. The compound of claim 17, wherein said polymer is poly(ethylene glycol).

30. The compound of claim 29, wherein said poly(ethylene glycol) has an average molecular weight from about 500 Da to about 100,000 Da.

31. The compound of claim 19, wherein G is a substituted or unsubstituted trityloxy group.

32. The compound of claim 31, wherein G is selected from a monoalkoxy substituted trityloxy group or dialkoxy substituted trityloxy group.

33. The compound of claim 19, wherein said group reactive with a biologically active molecule is selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide.

34. The compound of claim 19, wherein $R^2$ is absent or selected from the group consisting of trityl, monoalkoxytrityl, dialkoxytrityl, pixyl, alkoxypixyl, fluorenylmethyloxycarbonyl, alkylcarboxyl, benzoyl, tetrahydropyranyl, methyl.

35. The compound of claim 19, wherein said polymer is poly(ethylene glycol).

* * * * *